United States Patent
Kates

(10) Patent No.: US 7,142,123 B1
(45) Date of Patent: Nov. 28, 2006

(54) METHOD AND APPARATUS FOR DETECTING MOISTURE IN BUILDING MATERIALS

(76) Inventor: Lawrence Kates, 1111 Bayside Dr., Corona Del Mar, CA (US) 92625

( * ) Notice: Subject to any disclaimer, the term of this patent is extended or adjusted under 35 U.S.C. 154(b) by 0 days.

(21) Appl. No.: 11/233,931

(22) Filed: Sep. 23, 2005

(51) Int. Cl.
    *G08B 21/00* (2006.01)
(52) U.S. Cl. .................................. 340/602; 340/870.01
(58) Field of Classification Search ................. 340/602
    See application file for complete search history.

(56) References Cited

U.S. PATENT DOCUMENTS

| | | | |
|---|---|---|---|
| 4,099,168 A | 7/1978 | Kedjierski et al. | |
| 4,136,823 A | 1/1979 | Kullberg | |
| 4,226,533 A | 10/1980 | Snowman | |
| 4,266,220 A | 5/1981 | Malinowski | |
| 4,400,694 A | 8/1983 | Wong et al. | |
| 4,420,746 A | 12/1983 | Malinowski | |
| 4,455,553 A | 6/1984 | Johnson | |
| 4,535,450 A | 8/1985 | Tan | |
| 4,543,570 A | 9/1985 | Bressert et al. | |
| 4,556,873 A | 12/1985 | Yamada et al. | |
| 4,652,859 A | 3/1987 | Van Wienen | |
| 4,661,804 A | 4/1987 | Abel | |
| 4,670,739 A | 6/1987 | Kelly, Jr. | |
| 4,675,661 A | 6/1987 | Ishii | |
| 4,692,742 A | 9/1987 | Raizen et al. | |
| 4,692,750 A | 9/1987 | Murakami et al. | |
| 4,727,359 A | 2/1988 | Yuchi et al. | |
| 4,801,865 A * | 1/1989 | Miller et al. ................. | 340/602 |
| 4,827,244 A | 5/1989 | Bellavia et al. | |
| 4,862,514 A | 8/1989 | Kedjierski | |
| 4,871,999 A | 10/1989 | Ishii et al. | |
| 4,901,316 A | 2/1990 | Igarashi et al. | |
| 4,916,432 A | 4/1990 | Tice et al. | |

(Continued)

FOREIGN PATENT DOCUMENTS

EP        0 346 152 A2    12/1989

(Continued)

OTHER PUBLICATIONS

Vokey, David E et. al.; Moisture Detection Sensors For Building Structures. Feb. 3, 2005 WO 2005/010837 A2.*

(Continued)

*Primary Examiner*—Thomas Mullen
*Assistant Examiner*—Eric M. Blount
(74) *Attorney, Agent, or Firm*—Knobbe, Martens, Olson & Bear, LLP

(57) ABSTRACT

A moisture sensor system is described. In one embodiment, the system provides an adjustable threshold level for the sensed moisture level. The adjustable threshold allows the moisture sensor to adjust to ambient conditions, aging of components, and other operational variations while still providing a relatively sensitive detection capability. In one embodiment, the adjustable threshold moisture sensor is used in an intelligent sensor system that includes one or more intelligent sensor units and a base unit that can communicate with the moisture sensor units. When one or more of the moisture sensor units detects a excess moisture the moisture sensor unit communicates with the base unit and provides data regarding the moisture condition. The base unit can contact a supervisor or other responsible person by a plurality of techniques, such as, telephone, pager, cellular telephone, Internet (and/or local area network), etc. In one embodiment, one or more wireless repeaters are used between the moisture sensor units and the base unit to extend the range of the system and to allow the base unit to communicate with a larger number of sensors.

36 Claims, 25 Drawing Sheets

U.S. PATENT DOCUMENTS

| | | | |
|---|---|---|---|
| 4,977,527 A | 12/1990 | Shaw et al. | |
| 4,996,518 A | 2/1991 | Takahashi et al. | |
| 5,134,644 A | 7/1992 | Garton et al. | |
| 5,138,562 A | 8/1992 | Shaw et al. | |
| 5,151,683 A | 9/1992 | Takahashi et al. | |
| 5,159,315 A | 10/1992 | Schultz et al. | |
| 5,168,262 A | 12/1992 | Okayama | |
| 5,260,687 A | 11/1993 | Yamauchi et al. | |
| 5,267,180 A | 11/1993 | Okayama | |
| 5,281,951 A | 1/1994 | Okayama | |
| 5,319,698 A | 6/1994 | Glidewell et al. | |
| 5,345,224 A | 9/1994 | Brown | |
| 5,357,241 A | 10/1994 | Welch et al. | |
| 5,400,246 A | 3/1995 | Wilson et al. | |
| 5,430,433 A | 7/1995 | Shima | |
| 5,432,500 A | 7/1995 | Scripps | |
| 5,530,433 A | 6/1996 | Morita | |
| 5,568,121 A | 10/1996 | Lamensdorf | |
| 5,574,435 A | 11/1996 | Mochizuki | |
| 5,627,515 A | 5/1997 | Anderson | |
| 5,655,561 A | 8/1997 | Wendel et al. | |
| 5,736,928 A | 4/1998 | Tice et al. | |
| 5,748,092 A * | 5/1998 | Arsenault et al. | 340/602 |
| 5,854,994 A | 12/1998 | Canada et al. | |
| 5,859,536 A * | 1/1999 | Stockton | 324/664 |
| 5,881,951 A | 3/1999 | Carpenter | |
| 5,889,468 A | 3/1999 | Banga | |
| 5,907,491 A | 5/1999 | Canada et al. | |
| 5,949,332 A | 9/1999 | Kim | |
| 6,025,788 A * | 2/2000 | Diduck | 340/605 |
| 6,049,273 A | 4/2000 | Hess | |
| 6,060,994 A | 5/2000 | Chen | |
| 6,075,451 A | 6/2000 | Lebowitz et al. | |
| 6,078,050 A | 6/2000 | Castleman | |
| 6,078,269 A | 6/2000 | Markwell et al. | |
| 6,084,522 A | 7/2000 | Addy | |
| 6,097,288 A | 8/2000 | Koeppe, Jr. | |
| 6,175,310 B1 * | 1/2001 | Gott | 340/605 |
| 6,215,404 B1 | 4/2001 | Morales | |
| 6,313,646 B1 * | 11/2001 | Davis et al. | 324/690 |
| 6,320,501 B1 | 11/2001 | Tice et al. | |
| 6,369,714 B1 | 4/2002 | Walter | |
| 6,377,181 B1 * | 4/2002 | Kroll et al. | 340/602 |
| 6,380,860 B1 | 4/2002 | Goetz | |
| 6,420,973 B1 | 7/2002 | Acevedo | |
| 6,437,692 B1 | 8/2002 | Petite et al. | |
| 6,441,731 B1 | 8/2002 | Hess | |
| 6,445,292 B1 | 9/2002 | Jen et al. | |
| 6,515,283 B1 | 2/2003 | Castleman et al. | |
| 6,552,647 B1 | 4/2003 | Thiessen et al. | |
| 6,553,336 B1 | 4/2003 | Johnson et al. | |
| 6,583,720 B1 | 6/2003 | Quigley | |
| 6,704,681 B1 | 3/2004 | Nassof et al. | |
| 6,731,215 B1 * | 5/2004 | Harms et al. | 340/602 |
| 6,759,956 B1 | 7/2004 | Menard et al. | |
| 6,789,220 B1 | 9/2004 | Flanigan et al. | |
| 6,796,187 B1 * | 9/2004 | Srinivasan et al. | 73/784 |
| 6,995,676 B1 * | 2/2006 | Amacher | 340/602 |
| 2002/0011570 A1 | 1/2002 | Castleman | |
| 2002/0186141 A1 | 12/2002 | Jen et al. | |
| 2003/0058093 A1 | 3/2003 | Dohi et al. | |
| 2003/0199247 A1 | 10/2003 | Striemer | |
| 2005/0105841 A1 | 5/2005 | Luo et al. | |
| 2005/0116667 A1 | 6/2005 | Mueller et al. | |
| 2005/0131652 A1 | 6/2005 | Corwin et al. | |

FOREIGN PATENT DOCUMENTS

| | | |
|---|---|---|
| EP | 0 346 152 A3 | 12/1989 |
| WO | WO 00-21047 A1 | 4/2000 |

OTHER PUBLICATIONS

" Measuring and Controlling Indoor Humidity," http://www.relative-humidity-sensor.com, 3 pages.

Impedance Moisture Sensor Technology, http://www.sensorland.com/HowPage029.html, 2 pages.

"Relative Humidity Information," http://www.relative-humidity-sensor.com/relative-humidity.html, 6 pages.

"Ways to Prevent Mold Problems," http://www.toxic-black-mold-info.com/prevent.html, 12 pages.

"G-Cap™ 2 Relative Humidity Sensor," http://www.globalspec.com/FeaturedProducts/Detail?ExhibitID=1454, 2 pages.

Texas Instruments, Inc., Product catalog for "TRF6901 Single-Chip RF Transceiver," Copyright 2001-2003, 27 pages.

Texas Instruments, Inc., Mechanical Data for "PT (SPQFP-G48) Plastic Quad Flatpack," 2 pages.

* cited by examiner

SENSOR UNIT

METHOD AND APPARATUS FOR DETECTING MOISTURE IN BUILDING MATERIALS

BACKGROUND OF THE INVENTION

1. Field of the Invention

The present invention relates to a sensor system for detecting and determining the severity of moisture in building materials, such as wood, drywall, plaster, etc.

2. Description of the Related Art

Maintaining and protecting a building or complex is difficult and costly. Some conditions, such as fires, gas leaks, etc., are a danger to the occupants and the structure. Other malfunctions, such as moisture in roofs, plumbing, walls, etc., are not necessarily dangerous for the occupants, but can, nevertheless, cause considerable damage. In many cases, an adverse ambient condition such as water leakage, fire, etc., is not detected in the early stages when the damage and/or danger is relatively small. Sensors can be used to detect such adverse ambient conditions, but sensors present their own set of problems. For example, adding sensors, such as, for example, smoke detectors, water sensors, and the like in an existing structure can be prohibitively expensive due to the cost of installing wiring between the remote sensors and a centralized monitoring device used to monitor the sensors. Adding wiring to provide power to the sensors further increases the cost.

SUMMARY

The present invention solves these and other problems by providing a relatively low cost, robust, wireless sensor system that provides an extended period of operability without maintenance. The system includes one or more intelligent sensor units and a base unit that can communicate with the sensor units. When one or more of the sensor units detects an anomalous condition (e.g., moisture, smoke, fire, water, etc.) the sensor unit communicates with the base unit and provides data regarding the anomalous condition. The base unit can contact a supervisor or other responsible person by a plurality of techniques, such as, telephone, pager, cellular telephone, Internet (and/or local area network), etc. In one embodiment, one or more wireless repeaters are used between the sensor units and the base unit to extend the range of the system and to allow the base unit to communicate with a larger number of sensors.

In one embodiment, the sensor system includes a number of sensor units located throughout a building that sense conditions and report anomalous results back to a central reporting station. The sensor units measure conditions that might indicate a fire, water leak, etc. The sensor units report the measured data to the base unit whenever the sensor unit determines that the measured data is sufficiently anomalous to be reported. The base unit can notify a responsible person, such as, for example, a building manager, building owner, private security service, etc. In one embodiment, the sensor units do not send an alarm signal to the central location. Rather, the sensors send quantitative measured data (e.g., smoke density, temperature rate of rise, etc.) to the central reporting station.

In one embodiment, the sensor unit is placed in a building, apartment, office, residence, etc. In order to conserve battery power, the sensor is normally placed in a low-power mode. In one embodiment, while in low power mode, the sensor unit takes regular sensor readings and evaluates the readings to determine if an anomalous condition exists. If an anomalous condition is detected, then the sensor unit "wakes up" and begins communicating with the base unit or with a repeater. At programmed intervals, the sensor also "wakes up" and sends status information to the base unit (or repeater) and then listens for commands for a period of time.

In one embodiment, the sensor unit is bi-directional and configured to receive instructions from the central reporting station (or repeater). Thus, for example, the central reporting station can instruct the sensor to: perform additional measurements; go to a standby mode; wake up; report battery status; change wake-up interval; run self-diagnostics and report results; etc. In one embodiment, the sensor unit also includes a tamper switch. When tampering with the sensor is detected, the sensor reports such tampering to the base unit. In one embodiment, the sensor reports its general health and status to the central reporting station on a regular basis (e.g., results of self-diagnostics, battery health, etc.).

In one embodiment, the sensor unit provides two wake-up modes, a first wake-up mode for taking measurements (and reporting such measurements if deemed necessary), and a second wake-up mode for listening for commands from the central reporting station. The two wake-up modes, or combinations thereof, can occur at different intervals.

In one embodiment, the sensor units use spread-spectrum techniques to communicate with the base unit and/or the repeater units. In one embodiment, the sensor units use frequency-hopping spread-spectrum. In one embodiment, each sensor unit has an Identification code (ID) and the sensor units attaches its ID to outgoing communication packets. In one embodiment, when receiving wireless data, each sensor unit ignores data that is addressed to other sensor units.

The repeater unit is configured to relay communications traffic between a number of sensor units and the base unit. The repeater units typically operate in an environment with several other repeater units and thus, each repeater unit contains a database (e.g., a lookup table) of sensor IDs. During normal operation, the repeater only communicates with designated wireless sensor units whose IDs appears in the repeater's database. In one embodiment, the repeater is battery-operated and conserves power by maintaining an internal schedule of when it's designated sensors are expected to transmit and going to a low-power mode when none of its designated sensor units is scheduled to transmit. In one embodiment, the repeater uses spread-spectrum to communicate with the base unit and the sensor units. In one embodiment, the repeater uses frequency-hopping spread-spectrum to communicate with the base unit and the sensor units. In one embodiment, each repeater unit has an ID and the repeater unit attaches its ID to outgoing communication packets that originate in the repeater unit. In one embodiment, each repeater unit ignores data that is addressed to other repeater units or to sensor units not serviced by the repeater.

In one embodiment, the repeater is configured to provide bi-directional communication between one or more sensors and a base unit. In one embodiment, the repeater is configured to receive instructions from the central reporting station (or repeater). Thus, for example, the central reporting station can instruct the repeater to: send commands to one or more sensors; go to standby mode; "wake up"; report battery status; change wake-up interval; run self-diagnostics and report results; etc.

The base unit is configured to receive measured sensor data from a number of sensor units. In one embodiment, the sensor information is relayed through the repeater units. The base unit also sends commands to the repeater units and/or sensor units. In one embodiment, the base unit includes a diskless PC that runs off of a CD-ROM, flash memory, DVD, or other read-only device, etc. When the base unit receives data from a wireless sensor indicating that there may be an emergency condition (e.g., a fire or excess smoke, temperature, water, flammable gas, etc.) the base unit will attempt to notify a responsible party (e.g., a building manager) by several communication channels (e.g., telephone, Internet, pager, cell phone, etc.). In one embodiment, the base unit sends instructions to place the wireless sensor in an alert mode (inhibiting the wireless sensor's low-power mode). In one embodiment, the base unit sends instructions to activate one or more additional sensors near the first sensor.

In one embodiment, the base unit maintains a database of the health, battery status, signal strength, and current operating status of all of the sensor units and repeater units in the wireless sensor system. In one embodiment, the base unit automatically performs routine maintenance by sending commands to each sensor to run a self-diagnostic and report the results. The base unit collects such diagnostic results. In one embodiment, the base unit sends instructions to each sensor telling the sensor how long to wait between "wakeup" intervals. In one embodiment, the base unit schedules different wakeup intervals to different sensors based on the sensor's health, battery health, location, etc. In one embodiment, the base unit sends instructions to repeaters to route sensor information around a failed repeater.

In one embodiment, the sensor unit is configured to detect moisture in building materials such as, for example, drywall, wood, plaster, concrete, etc. In one embodiment, two or more conductors are provided in proximity to the building material. The conductors are provided to a sensor unit.

In one embodiment, a relatively low cost, robust, moisture sensor system that provides an adjustable threshold level for the sensed moisture level. The adjustable threshold allows the moisture sensor to adjust to ambient conditions, aging of components, and other operational variations while still providing a relatively sensitive detection capability for hazardous conditions. The adjustable threshold moisture sensor can operate for an extended period of operability without maintenance or recalibration. In one embodiment, the moisture sensor is self-calibrating and runs through a calibration sequence at startup or at periodic intervals. In one embodiment, the adjustable threshold moisture sensor is used in an intelligent sensor system that includes one or more intelligent sensor units and a base unit that can communicate with the moisture sensor units. When one or more of the moisture sensor units detects an anomalous condition (e.g., moisture, fire, water, etc.) the moisture sensor unit communicates with the base unit and provides data regarding the anomalous condition. The base unit can contact a supervisor or other responsible person by a plurality of techniques, such as, telephone, pager, cellular telephone, Internet (and/or local area network), etc. In one embodiment, one or more wireless repeaters are used between the moisture sensor units and the base unit to extend the range of the system and to allow the base unit to communicate with a larger number of sensors.

In one embodiment, the adjustable-threshold moisture sensor sets a threshold level according to an average value of the moisture sensor reading. In one embodiment, the average value is a relatively long-term average. In one embodiment, the average is a time-weighted average wherein recent sensor readings used in the averaging process are weighted differently than less recent sensor readings. The average is used to set the threshold level. When the moisture sensor reading rises above the threshold level, the moisture sensor indicates an alarm condition. In one embodiment, the moisture sensor indicates an alarm condition when the moisture sensor reading rises above the threshold value for a specified period of time. In one embodiment, the moisture sensor indicates an alarm condition when a statistical number of sensor readings (e.g., 3 of 2, 5 of 3, 10 of 7, etc.) are above the threshold level. In one embodiment, the moisture sensor indicates various levels of alarm (e.g., notice, alert, alarm) based on how far above the threshold the moisture sensor reading has risen and/or how rapidly the moisture sensor reading has risen.

In one embodiment, the moisture sensor system includes a number of sensor units located throughout a building that sense conditions and report anomalous results back to a central reporting station. The moisture sensor units measure conditions that might indicate a fire, water leak, etc. The moisture sensor units report the measured data to the base unit whenever the moisture sensor unit determines that the measured data is sufficiently anomalous to be reported. The base unit can notify a responsible person such as, for example, a building manager, building owner, private security service, etc. In one embodiment, the moisture sensor units do not send an alarm signal to the central location. Rather, the moisture sensors send quantitative measured data (e.g., moisture, rate of rise, length of time, etc.) to the central reporting station.

In one embodiment, the moisture sensor system includes a battery-operated sensor unit that detects moisture in building materials. The moisture sensor unit is placed in a building, apartment, office, residence, etc., and provided to a moisture probe. In order to conserve battery power, the moisture sensor is normally placed in a low-power mode. In one embodiment, while in the low-power mode, the moisture sensor unit takes regular sensor readings, adjusts the threshold level, and evaluates the readings to determine if an anomalous condition exists. If an anomalous condition is detected, then the moisture sensor unit "wakes up" and begins communicating with the base unit or with a repeater. At programmed intervals, the moisture sensor also "wakes up" and sends status information to the base unit (or repeater) and then listens for commands for a period of time.

DETAILED DESCRIPTION

Figure 1:
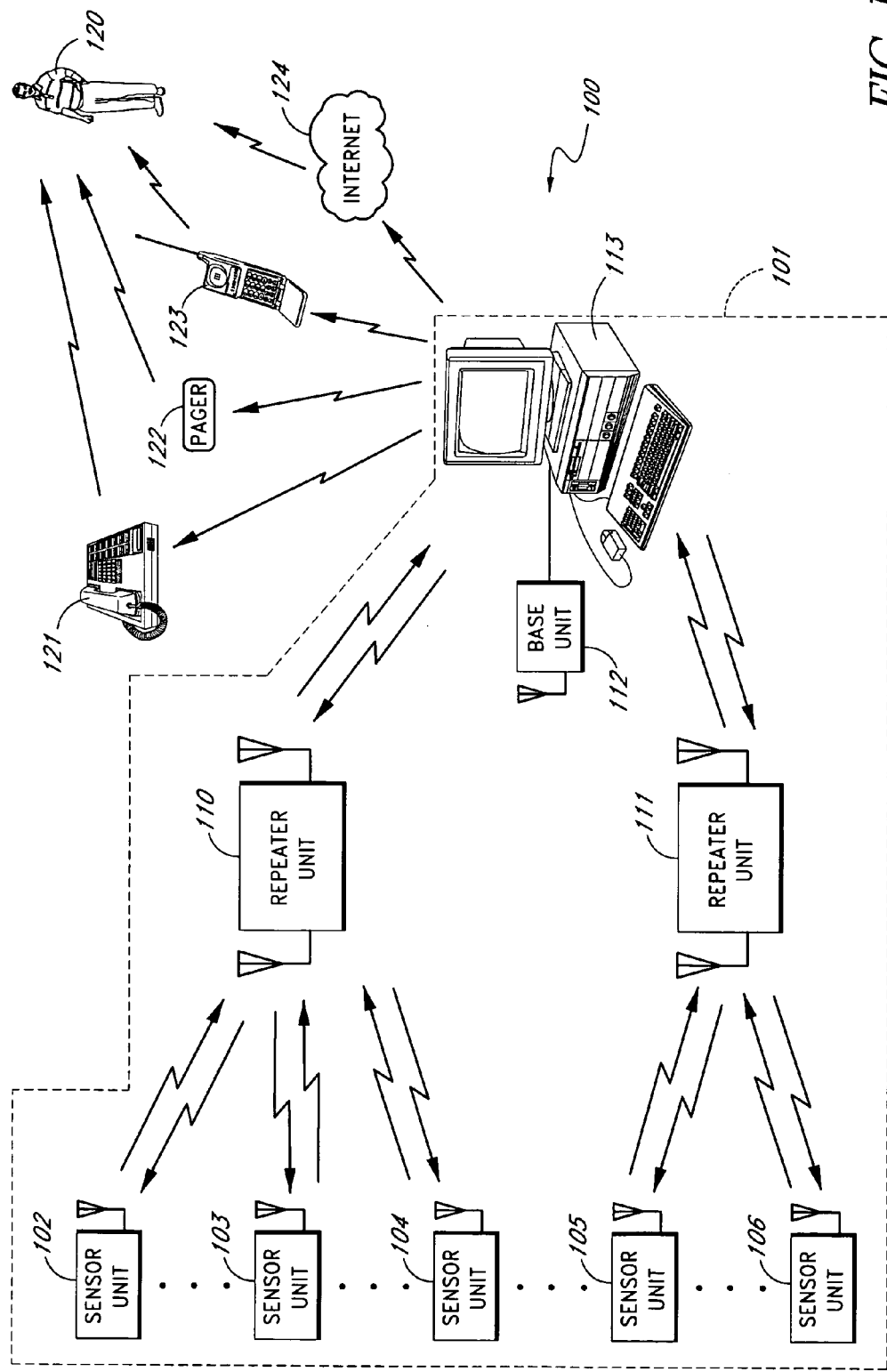
FIG. 1 shows a sensor system that includes a plurality of sensor units that communicate with a base unit through a number of repeater units.

FIG. 1 shows a sensor system 100 that includes a plurality of sensor units 102–106 that communicate with a base unit 112 through a number of repeater units 110–111. The sensor units 102–106 are located throughout a building 101. Sensor units 102–104 communicate with the repeater 110. Sensor units 105–106 communicate with the repeater 111. The repeaters 110–111 communicate with the base unit 112. The base unit 112 communicates with a monitoring computer system 113 through a computer network connection such as, for example, Ethernet, wireless Ethernet, firewire port, Universal Serial Bus (USB) port, bluetooth, etc. The computer system 113 contacts a building manager, maintenance service, alarm service, or other responsible personnel 120 using one or more of several communication systems such as, for example, telephone 121, pager 122, cellular telephone 123 (e.g., direct contact, voicemail, text, etc.), and/or through the Internet and/or local area network 124 (e.g., through email, instant messaging, network communications, etc.). In one embodiment, multiple base units 112 are provided to the monitoring computer 113. In one embodiment, the monitoring computer 113 is provided to more than one computer monitor, thus, allowing more data to be displayed than can conveniently be displayed on a single monitor. In one embodiment, the monitoring computer 113 is provided to multiple monitors located in different locations, thus, allowing the data from the monitoring computer 113 to be displayed in multiple locations.

The sensor units 102–106 include sensors to measure conditions, such as, for example, smoke, temperature, moisture, water, water temperature, humidity, carbon monoxide, natural gas, propane gas, security alarms, intrusion alarms (e.g., open doors, broken windows, open windows, and the like), other flammable gases, radon, poison gases, etc. Different sensor units can be configured with different sensors or with combinations of sensors. Thus, for example, in one installation the sensor units 102 and 104 could be configured with smoke and/or temperature sensors while the sensor unit 103 could be configured with a humidity sensor.

The discussion that follows generally refers to the sensor unit 102 as an example of a sensor unit, with the understanding that the description of the sensor unit 102 can be applied to many sensor units. Similarly, the discussion generally refers to the repeater 110 by way of example, and not limitation. It will also be understood by one of ordinary skill in the art that repeaters are useful for extending the range of the sensor units 102–106 but are not required in all embodiments. Thus, for example in one embodiment, one or more of the sensor units 102–106 can communicate directly with the base unit 112 without going through a repeater. It will also be understood by one of ordinary skill in the art that FIG. 1 shows only five sensor units (102–106) and two repeater units (110–111) for purposes of illustration and not by way of limitation. An installation in a large apartment building or complex would typically involve many sensor units and repeater units. Moreover, one of ordinary skill in the art will recognize that one repeater unit can service relatively many sensor units. In one embodiment, the sensor unit 102 can communicate directly with the base unit 112 without going through a repeater 111.

When the sensor unit 102 detects an anomalous condition (e.g., smoke, fire, water, etc.) the sensor unit communicates with the appropriate repeater unit 110 and provides data regarding the anomalous condition. The repeater unit 110 forwards the data to the base unit 112, and the base unit 112 forwards the information to the computer 113. The computer 113 evaluates the data and takes appropriate action. If the computer 113 determines that the condition is an emergency (e.g., fire, smoke, large quantities of water), then the computer 113 contacts the appropriate personnel 120. If the computer 113 determines that the situation warrants reporting, but is not an emergency, then the computer 113 logs the data for later reporting. In this way, the sensor system 100 can monitor the conditions in and around the building 101.

In one embodiment, the sensor unit 102 has an internal power source (e.g., battery, solar cell, fuel cell, etc.). In order to conserve power, the sensor unit 102 is normally placed in a low-power mode. In one embodiment, using sensors that require relatively little power, while in the low power mode the sensor unit 102 takes regular sensor readings and evaluates the readings to determine if an anomalous condition exists. In one embodiment, using sensors that require relatively more power, while in the low power mode the sensor unit 102 takes and evaluates sensor readings at periodic intervals. If an anomalous condition is detected, then the sensor unit 102 "wakes up" and begins communicating with the base unit 112 through the repeater 110. At programmed intervals, the sensor unit 102 also "wakes up" and sends status information (e.g., power levels, self diagnostic information, etc.) to the base unit (or repeater) and then listens for commands for a period of time. In one embodiment, the sensor unit 102 also includes a tamper detector. When tampering with the sensor unit 102 is detected, the sensor unit 102 reports such tampering to the base unit 112.

In one embodiment, the sensor unit 102 provides bi-directional communication and is configured to receive data and/or instructions from the base unit 112. Thus, for example, the base unit 112 can instruct the sensor unit 102 to perform additional measurements, to go to a standby mode, to wake up, to report battery status, to change wake-up interval, to run self-diagnostics and report results, etc. In one embodiment, the sensor unit 102 reports its general health and status on a regular basis (e.g., results of self-diagnostics, battery health, etc.)

In one embodiment, the sensor unit 102 provides two wake-up modes, a first wake-up mode for taking measurements (and reporting such measurements if deemed necessary), and a second wake-up mode for listening for commands from the central reporting station. The two wake-up modes, or combinations thereof, can occur at different intervals.

In one embodiment, the sensor unit 102 uses spread-spectrum techniques to communicate with the repeater unit 110. In one embodiment, the sensor unit 102 use frequency-hopping spread-spectrum. In one embodiment, the sensor unit 102 has an address or identification (ID) code that distinguishes the sensor unit 102 from the other sensor units. The sensor unit 102 attaches its ID to outgoing communication packets so that transmissions from the sensor unit 102 can be identified by the repeater 110. The repeater 110 attaches the ID of the sensor unit 102 to data and/or instructions that are transmitted to the sensor unit 102. In one embodiment, the sensor unit 102 ignores data and/or instructions that are addressed to other sensor units.

In one embodiment, the sensor unit 102 includes a reset function. In one embodiment, the reset function is activated by the reset switch 208. In one embodiment, the reset function is active for a prescribed interval of time. During the reset interval, the transceiver 203 is in a receiving mode and can receive the identification code from an external programmer. In one embodiment, the external programmer wirelessly transmits a desired identification code. In one embodiment, the identification code is programmed by an external programmer that is connected to the sensor unit 102 through an electrical connector. In one embodiment, the electrical connection to the sensor unit 102 is provided by sending modulated control signals (power line carrier signals) through a connector used to connect the power source 206. In one embodiment, the external programmer provides power and control signals. In one embodiment, the external programmer also programs the type of sensor(s) installed in the sensor unit. In one embodiment, the identification code includes an area code (e.g., apartment number, zone number, floor number, etc.) and a unit number (e.g., unit 1, 2, 3, etc.).

In one embodiment, the external programmer interfaces with the controller 202 by using an optional programming interface 210. In one embodiment, the programming interface 210 includes a connector. In one embodiment, the programming interface 210 includes an infrared interface. In one embodiment, the programming interface 210 includes an inductive coupling coil. In one embodiment, the programming interface 210 includes one or more capacitive coupling plates.

In one embodiment, the sensor communicates with the repeater on the 900 MHz band. This band provides good transmission through walls and other obstacles normally found in and around a building structure. In one embodiment, the sensor communicates with the repeater on bands above and/or below the 900 MHz band. In one embodiment, the sensor, repeater, and/or base unit listen to a radio frequency channel before transmitting on that channel or before beginning transmission. If the channel is in use, (e.g., by another device such as another repeater, a cordless telephone, etc.) then the sensor, repeater and/or base unit changes to a different channel. In one embodiment, the sensor, repeater and/or base unit coordinate frequency hopping by listening to radio frequency channels for interference and using an algorithm to select a next channel for transmission that avoids the interference. Thus, for example, in one embodiment, if a sensor senses a dangerous condition and goes into a continuous transmission mode, the sensor will test (e.g., listen to) the channel before transmission to avoid channels that are blocked, in use, or jammed. In one embodiment, the sensor continues to transmit data until it receives an acknowledgement from the base unit that the message has been received. In one embodiment, the sensor transmits data having a normal priority (e.g., status information) and does not look for an acknowledgement, and the sensor transmits data having elevated priority (e.g., excess smoke, temperature, etc.) until an acknowledgement is received.

The repeater unit 110 is configured to relay communications traffic between the sensor 102 (and, similarly, the sensor units 103–104) and the base unit 112. The repeater unit 110 typically operates in an environment with several other repeater units (such as the repeater unit 111 in FIG. 1) and thus, the repeater unit 110 contains a database (e.g., a lookup table) of sensor unit IDs. In FIG. 1, the repeater 110 has database entries for the Ids of the sensors 102–104, and thus, the sensor 110 will only communicate with sensor units 102–104. In one embodiment, the repeater 110 has an internal power source (e.g., battery, solar cell, fuel cell, etc.) and conserves power by maintaining an internal schedule of when the sensor units 102–104 are expected to transmit. In one embodiment, the repeater unit 110 goes to a low-power mode when none of its designated sensor units is scheduled to transmit. In one embodiment, the repeater 110 uses spread-spectrum techniques to communicate with the base unit 112 and with the sensor units 102–104. In one embodiment, the repeater 110 uses frequency-hopping spread-spectrum to communicate with the base unit 112 and the sensor units 102–104. In one embodiment, the repeater unit 110 has an address or identification (ID) code and the repeater unit 110 attaches its address to outgoing communication packets that originate in the repeater (that is, packets that are not being forwarded). In one embodiment, the repeater unit 110 ignores data and/or instructions that are addressed to other repeater units or to sensor units not serviced by the repeater 110.

In one embodiment, the base unit 112 communicates with the sensor unit 102 by transmitting a communication packet addressed to the sensor unit 102. The repeaters 110 and 111 both receive the communication packet addressed to the sensor unit 102. The repeater unit 111 ignores the communication packet addressed to the sensor unit 102. The repeater unit 110 transmits the communication packet addressed to the sensor unit 102 to the sensor unit 102. In one embodiment, the sensor unit 102, the repeater unit 110, and the base unit 112 communicate using Frequency-Hopping Spread Spectrum (FHSS), also known as channel-hopping.

Frequency-hopping wireless systems offer the advantage of avoiding other interfering signals and avoiding collisions.

Moreover, there are regulatory advantages given to systems that do not transmit continuously at one frequency. Channel-hopping transmitters change frequencies after a period of continuous transmission, or when interference is encountered. These systems may have higher transmit power and relaxed limitations on in-band spurs. FCC regulations limit transmission time on one channel to 400 milliseconds (averaged over 10–20 seconds depending on channel bandwidth) before the transmitter must change frequency. There is a minimum frequency step when changing channels to resume transmission. If there are 25 to 49 frequency channels, regulations allow effective radiated power of 24 dBm, spurs must be −20 dBc, and harmonics must be −41.2 dBc. With 50 or more channels, regulations allow effective radiated power to be up to 30 dBm.

In one embodiment, the sensor unit 102, the repeater unit 110, and the base unit 112 communicate using FHSS wherein the frequency hopping of the sensor unit 102, the repeater unit 110, and the base unit 112 are not synchronized such that at any given moment, the sensor unit 102 and the repeater unit 110 are on different channels. In such a system, the base unit 112 communicates with the sensor unit 102 using the hop frequencies synchronized to the repeater unit 110 rather than the sensor unit 102. The repeater unit 110 then forwards the data to the sensor unit using hop frequencies synchronized to the sensor unit 102. Such a system largely avoids collisions between the transmissions by the base unit 112 and the repeater unit 110.

In one embodiment, the sensor units 102–106 all use FHSS and the sensor units 102–106 are not synchronized. Thus, at any given moment, it is unlikely that any two or more of the sensor units 102–106 will transmit on the same frequency. In this manner, collisions are largely avoided. In one embodiment, collisions are not detected but are tolerated by the system 100. If a collision does occur, data lost due to the collision is effectively re-transmitted the next time the sensor units transmit sensor data. When the sensor units 102–106 and repeater units 110–111 operate in asynchronous mode, then a second collision is highly unlikely because the units causing the collisions have hopped to different channels. In one embodiment, the sensor units 102–106, repeater units 110–111, and the base unit 112 use the same hop rate. In one embodiment, the sensor units 102–106, repeater units 110–111, and the base unit 112 use the same pseudo-random algorithm to control channel hopping, but with different starting seeds. In one embodiment, the starting seed for the hop algorithm is calculated from the ID of the sensor units 102–106, repeater units 110–111, or the base unit 112.

In an alternative embodiment, the base unit communicates with the sensor unit 102 by sending a communication packet addressed to the repeater unit 110, where the packet sent to the repeater unit 110 includes the address of the sensor unit 102. The repeater unit 102 extracts the address of the sensor unit 102 from the packet and creates and transmits a packet addressed to the sensor unit 102.

In one embodiment, the repeater unit 110 is configured to provide bi-directional communication between its sensors and the base unit 112. In one embodiment, the repeater 110 is configured to receive instructions from the base unit 110. Thus, for example, the base unit 112 can instruct the repeater to: send commands to one or more sensors; go to standby mode; "wake up"; report battery status; change wake-up interval; run self-diagnostics and report results; etc.

The base unit 112 is configured to receive measured sensor data from a number of sensor units either directly, or through the repeaters 110–111. The base unit 112 also sends commands to the repeater units 110–111 and/or to the sensor units 102–106. In one embodiment, the base unit 112 communicates with a diskless computer 113 that runs off of a CD-ROM. When the base unit 112 receives data from sensor units 102–106 indicating that there may be an emergency condition (e.g., a fire or excess smoke, temperature, water, etc.) the computer 113 will attempt to notify the responsible party 120.

In one embodiment, the computer 113 maintains a database of the health, power status (e.g., battery charge), and current operating status of all of the sensor units 102–106 and the repeater units 110–111. In one embodiment, the computer 113 automatically performs routine maintenance by sending commands to each sensor unit 102–106 to run a self-diagnostic and report the results. The computer 113 collects and logs such diagnostic results. In one embodiment, the computer 113 sends instructions to each sensor units 102–106 telling the sensor how long to wait between "wakeup" intervals. In one embodiment, the computer 113 schedules different wakeup intervals to different sensor units 102–106 based on the sensor unit's health, power status, location, etc. In one embodiment, the computer 113 schedules different wakeup intervals to different sensor unit 102–106 based on the type of data and urgency of the data collected by the sensor unit (e.g., sensor units that have smoke and/or temperature sensors produce data that should be checked relatively more often than sensor units that have humidity or moisture sensors). In one embodiment, the base unit sends instructions to repeaters to route sensor information around a failed repeater.

In one embodiment, the computer 113 produces a display that tells maintenance personnel which sensor units 102–106 need repair or maintenance. In one embodiment, the computer 113 maintains a list showing the status and/or location of each sensor according to the ID of each sensor.

In one embodiment, the sensor units 102–106 and/or the repeater units 110–111 measure the signal strength of the wireless signals received (e.g., the sensor unit 102 measures the signal strength of the signals received from the repeater unit 110, the repeater unit 110 measures the signal strength received from the sensor unit 102 and/or the base unit 112). The sensor units 102–106 and/or the repeater units 110–111 report such signal strength measurement back to the computer 113. The computer 113 evaluates the signal strength measurements to ascertain the health and robustness of the sensor system 100. In one embodiment, the computer 113 uses the signal strength information to re-route wireless communications traffic in the sensor system 100. Thus, for example, if the repeater unit 110 goes offline or is having difficulty communicating with the sensor unit 102, the computer 113 can send instructions to the repeater unit 111 to add the ID of the sensor unit 102 to the database of the repeater unit 111 (and similarly, send instructions to the repeater unit 110 to remove the ID of the sensor unit 102), thereby routing the traffic for the sensor unit 102 through the router unit 111 instead of the router unit 110.

Figure 2:
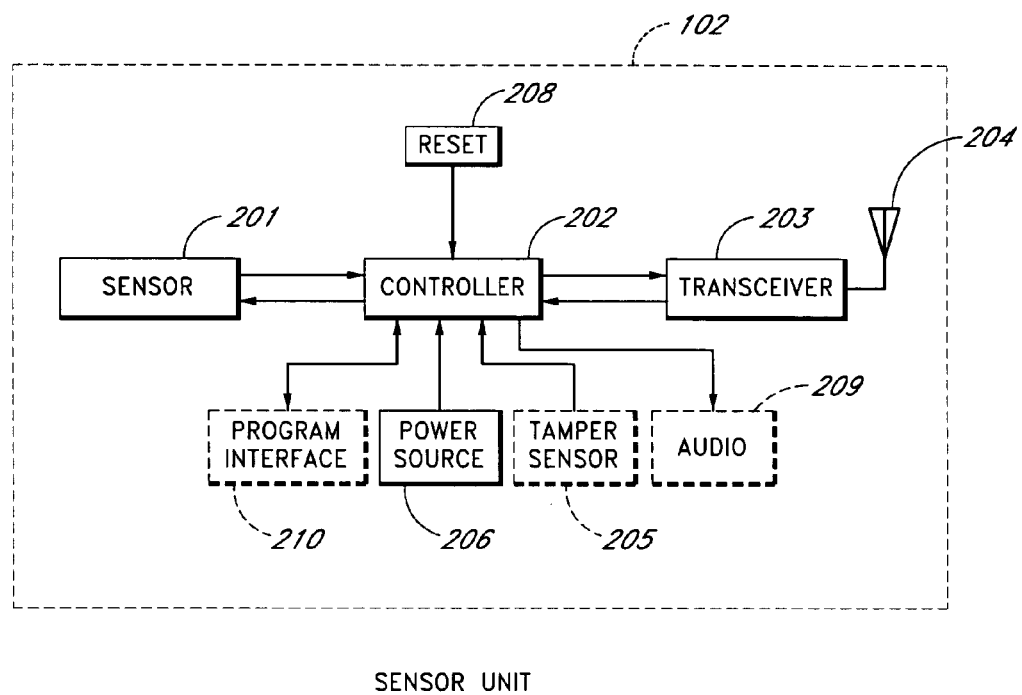
FIG. 2 is a block diagram of a sensor unit.

FIG. 2 is a block diagram of the sensor unit 102. In the sensor unit 102, one or more sensors 201 and a transceiver 203 are provided to a controller 202. The controller 202 typically provides power, data, and control information to the sensor(s) 201 and the transceiver 203. A power source 206 is provided to the controller 202. An optional tamper sensor 205 is also provided to the controller 202. A reset device (e.g., a switch) 208 is proved to the controller 202. In one embodiment, an optional audio output device 209 is provided. In one embodiment, the sensor 201 is configured as a plug-in module that can be replaced relatively easily.

In one embodiment, the transceiver 203 is based on a TRF 6901 transceiver chip from Texas Instruments. Inc. In one embodiment, the controller 202 is a conventional programmable microcontroller. In one embodiment, the controller 202 is based on a Field Programmable Gate Array (FPGA), such as, for example, provided by Xilinx Corp. In one embodiment, the sensor 201 includes an optoelectric smoke sensor with a smoke chamber. In one embodiment, the sensor 201 includes a thermistor. In one embodiment, the sensor 201 includes a humidity sensor. In one embodiment, the sensor 201 includes a sensor, such as, for example, a water level sensor, a water temperature sensor, a carbon monoxide sensor, a moisture sensor, a water flow sensor, natural gas sensor, propane sensor, etc.

The controller 202 receives sensor data from the sensor(s) 201. Some sensors 201 produce digital data. However, for many types of sensors 201, the sensor data is analog data. Analog sensor data is converted to digital format by the controller 202. In one embodiment, the controller evaluates the data received from the sensor(s) 201 and determines whether the data is to be transmitted to the base unit 112. The sensor unit 102 generally conserves power by not transmitting data that falls within a normal range. In one embodiment, the controller 202 evaluates the sensor data by comparing the data value to a threshold value (e.g., a high threshold, a low threshold, or a high-low threshold). If the data is outside the threshold (e.g., above a high threshold, below a low threshold, outside an inner range threshold, or inside an outer range threshold), then the data is deemed to be anomalous and is transmitted to the base unit 112. In one embodiment, the data threshold is programmed into the controller 202. In one embodiment, the data threshold is programmed by the base unit 112 by sending instructions to the controller 202. In one embodiment, the controller 202 obtains sensor data and transmits the data when commanded by the computer 113.

In one embodiment, the tamper sensor 205 is configured as a switch that detects removal of or tampering with the sensor unit 102.

Figure 3:
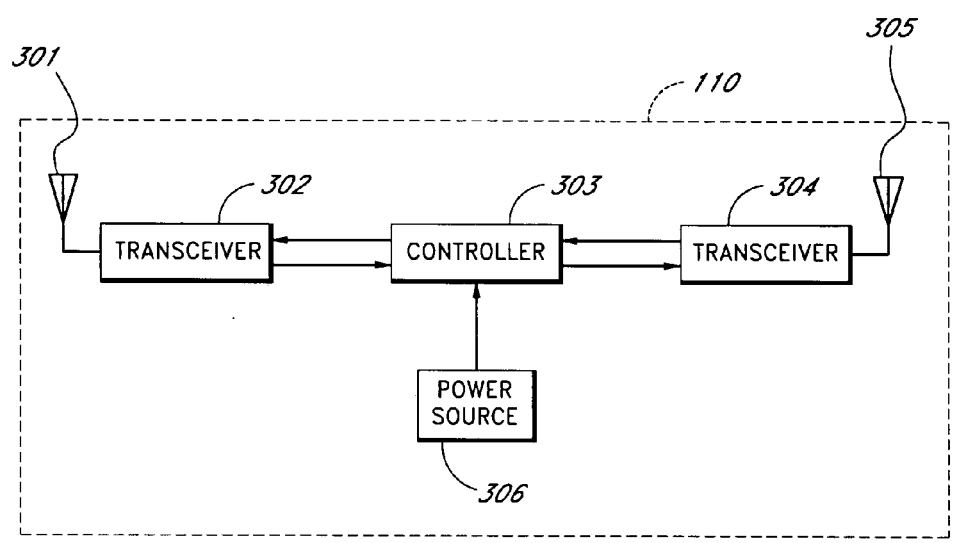
FIG. 3 is a block diagram of a repeater unit.

FIG. 3 is a block diagram of the repeater unit 110. In the repeater unit 110, a first transceiver 302 and a second transceiver 304 are provided to a controller 303. The controller 303 typically provides power, data, and control information to the transceivers 302, 304. A power source 306 is provided to the controller 303. An optional tamper sensor (not shown) is also provided to the controller 303.

When relaying sensor data to the base unit 112, the controller 303 receives data from the first transceiver 302 and provides the data to the second transceiver 304. When relaying instructions from the base unit 112 to a sensor unit, the controller 303 receives data from the second transceiver 304 and provides the data to the first transceiver 302. In one embodiment, the controller 303 conserves power by powering-down the transceivers 302, 304 during periods when the controller 303 is not expecting data. The controller 303 also monitors the power source 306 and provides status information, such as, for example, self-diagnostic information and/or information about the health of the power source 306, to the base unit 112. In one embodiment, the controller 303 sends status information to the base unit 112 at regular intervals. In one embodiment, the controller 303 sends status information to the base unit 112 when requested by the base unit 112. In one embodiment, the controller 303 sends status information to the base unit 112 when a fault condition (e.g., battery low) is detected.

In one embodiment, the controller 303 includes a table or list of identification codes for wireless sensor units 102. The repeater 110 forwards packets received from, or sent to, sensor units 102 in the list. In one embodiment, the repeater 110 receives entries for the list of sensor units from the computer 113. In one embodiment, the controller 303 determines when a transmission is expected from the sensor units 102 in the table of sensor units and places the repeater 110 (e.g., the transceivers 302, 304) in a low-power mode when no transmissions are expected from the transceivers on the list. In one embodiment, the controller 303 recalculates the times for low-power operation when a command to change reporting interval is forwarded to one of the sensor units 102 in the list (table) of sensor units or when a new sensor unit is added to the list (table) of sensor units.

Figure 4:
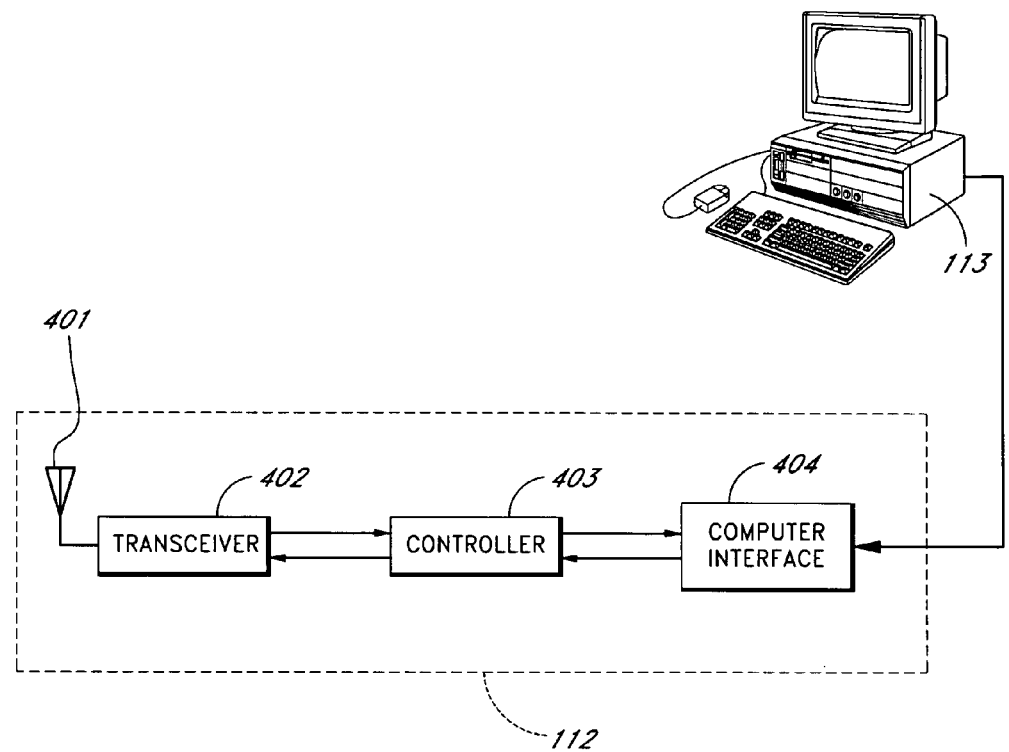
FIG. 4 is a block diagram of the base unit.

FIG. 4 is a block diagram of the base unit 112. In the base unit 112, a transceiver 402 and a computer interface 404 are provided to a controller 403. The controller 403 typically provides data and control information to the transceivers 402 and to the interface. The interface 404 is provided to a port on the monitoring computer 113. The interface 404 can be a standard computer data interface, such as, for example, Ethernet, wireless Ethernet, firewire port, Universal Serial Bus (USB) port, bluetooth, etc.

Figure 5:
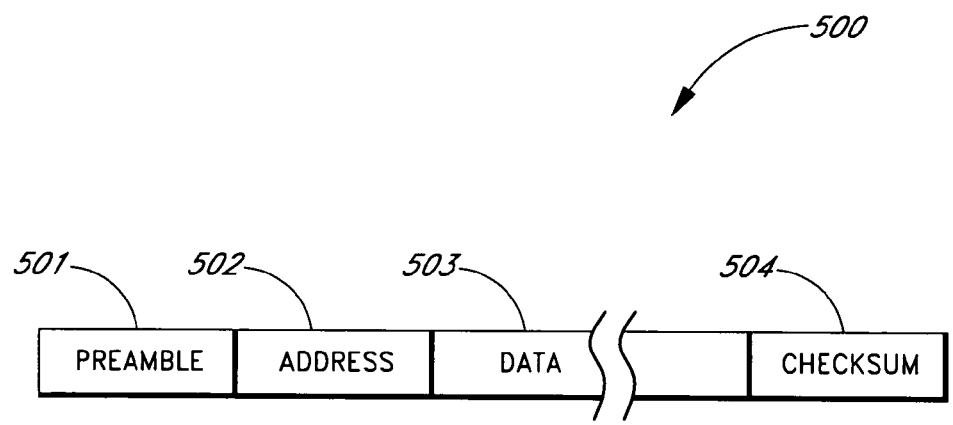
FIG. 5 shows one embodiment of a network communication packet used by the sensor units, repeater units, and the base unit.

FIG. 5 shows one embodiment of a communication packet 500 used by the sensor units, repeater units, and the base unit. The packet 500 includes a preamble portion 501, an address (or ID) portion 502, a data payload portion 503, and an integrity portion 504. In one embodiment, the integrity portion 504 includes a checksum. In one embodiment, the sensor units 102–106, the repeater units 110–111, and the base unit 112 communicate using packets such as the packet 500. In one embodiment, the packets 500 are transmitted using FHSS.

In one embodiment, the data packets that travel between the sensor unit 102, the repeater unit 111, and the base unit 112 are encrypted. In one embodiment, the data packets that travel between the sensor unit 102, the repeater unit 111, and the base unit 112 are encrypted and an authentication code is provided in the data packet so that the sensor unit 102, the repeater unit, and/or the base unit 112 can verify the authenticity of the packet.

In one embodiment the address portion 502 includes a first code and a second code. In one embodiment, the repeater 111 only examines the first code to determine if the packet should be forwarded. Thus, for example, the first code can be interpreted as a building (or building complex) code and the second code interpreted as a subcode (e.g., an apartment code, area code, etc.). A repeater that uses the first code for forwarding, thus, forwards packets having a specified first code (e.g., corresponding to the repeater's building or building complex). Thus, alleviates the need to program a list of sensor units 102 into a repeater, since a group of sensors in a building will typically all have the same first code but different second codes. A repeater so configured, only needs to know the first code to forward packets for any repeater in the building or building complex. This does, however, raise the possibility that two repeaters in the same building could try to forward packets for the same sensor unit 102. In one embodiment, each repeater waits for a programmed delay period before forwarding a packet. Thus reducing the chance of packet collisions at the base unit (in the case of sensor unit to base unit packets) and reducing the chance of packet collisions at the sensor unit (in the case of base unit to sensor unit packets). In one embodiment, a delay period is programmed into each repeater. In one embodiment, delay periods are pre-programmed onto the repeater units at the factory or during installation. In one embodiment, a delay period is programmed into each repeater by the base unit 112. In one embodiment, a repeater randomly chooses a delay period. In one embodiment, a repeater randomly chooses a delay period for each forwarded packet. In one embodiment, the first code is at least 6 digits. In one embodiment, the second code is at least 5 digits.

In one embodiment, the first code and the second code are programmed into each sensor unit at the factory. In one embodiment, the first code and the second code are programmed when the sensor unit is installed. In one embodiment, the base unit 112 can re-program the first code and/or the second code in a sensor unit.

In one embodiment, collisions are further avoided by configuring each repeater unit 111 to begin transmission on a different frequency channel. Thus, if two repeaters attempt to begin transmission at the same time, the repeaters will not interfere with each other because the transmissions will begin on different channels (frequencies).

Figure 6:
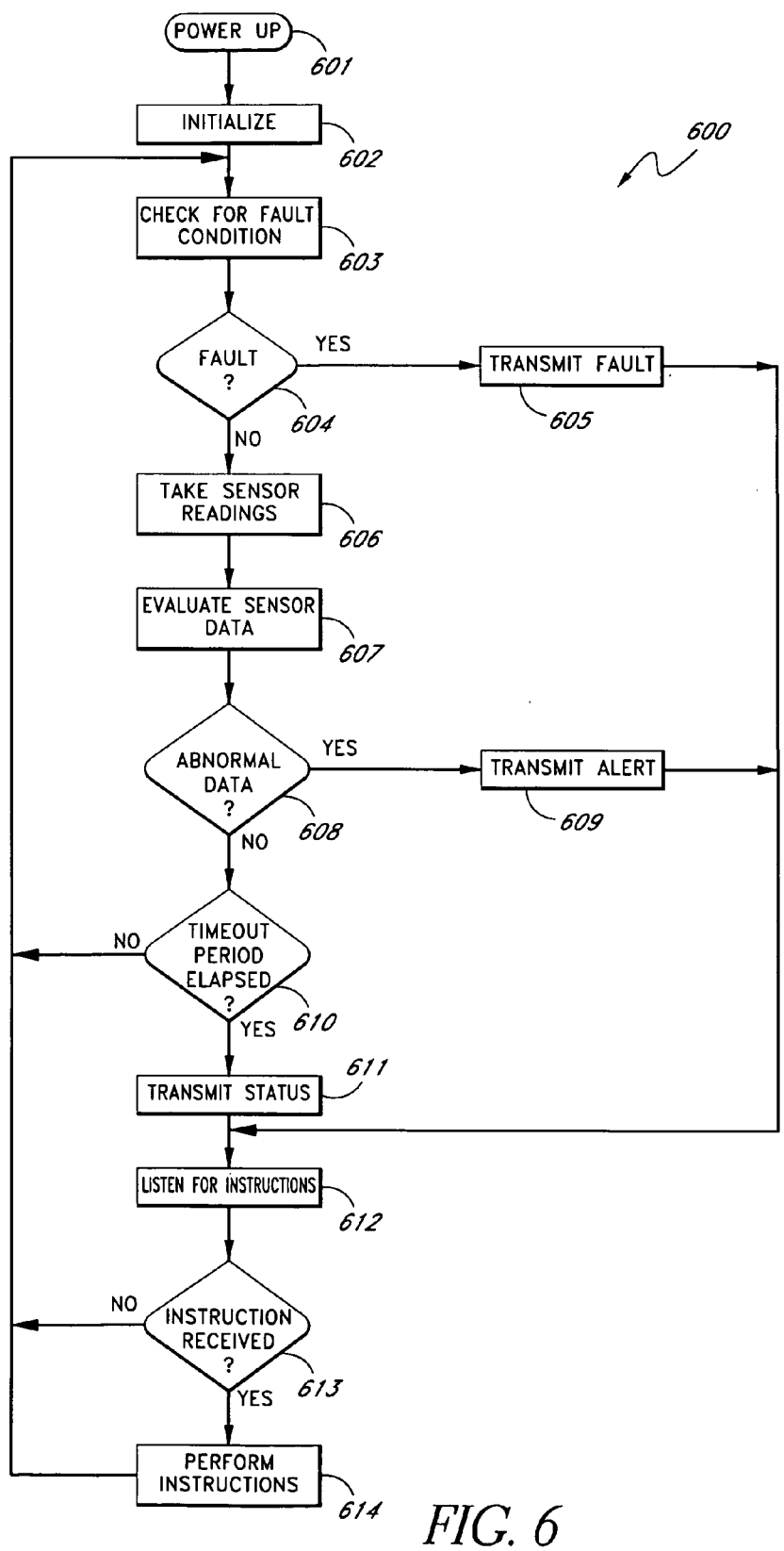
FIG. 6 is a flowchart showing operation of a sensor unit that provides relatively continuous monitoring.

FIG. 6 is a flowchart showing one embodiment of the operation of the sensor unit 102 wherein relatively continuous monitoring is provided. In FIG. 6, a power up block 601 is followed by an initialization block 602. After initialization, the sensor unit 102 checks for a fault condition (e.g., activation of the tamper sensor, low battery, internal fault, etc.) in a block 603. A decision block 604 checks the fault status. If a fault has occurred, then the process advances to a block 605 were the fault information is transmitted to the repeater 110 (after which, the process advances to a block 612); otherwise, the process advances to a block 606. In the block 606, the sensor unit 102 takes a sensor reading from the sensor(s) 201. The sensor data is subsequently evaluated in a block 607. If the sensor data is abnormal, then the process advances to a transmit block 609 where the sensor data is transmitted to the repeater 110 (after which, the process advances to a block 612); otherwise, the process advances to a timeout decision block 610. If the timeout period has not elapsed, then the process returns to the fault-check block 603; otherwise, the process advances to a transmit status block 611 where normal status information is transmitted to the repeater 110. In one embodiment, the normal status information transmitted is analogous to a simple "ping" which indicates that the sensor unit 102 is functioning normally. After the block 611, the process proceeds to a block 612 where the sensor unit 102 momentarily listens for instructions from the monitor computer 113. If an instruction is received, then the sensor unit 102 performs the instructions, otherwise, the process returns to the status check block 603. In one embodiment, transceiver 203 is normally powered down. The controller 202 powers up the transceiver 203 during execution of the blocks 605, 609, 611, and 612. The monitoring computer 113 can send instructions to the sensor unit 102 to change the parameters used to evaluate data used in block 607, the listen period used in block 612, etc.

Figure 7:
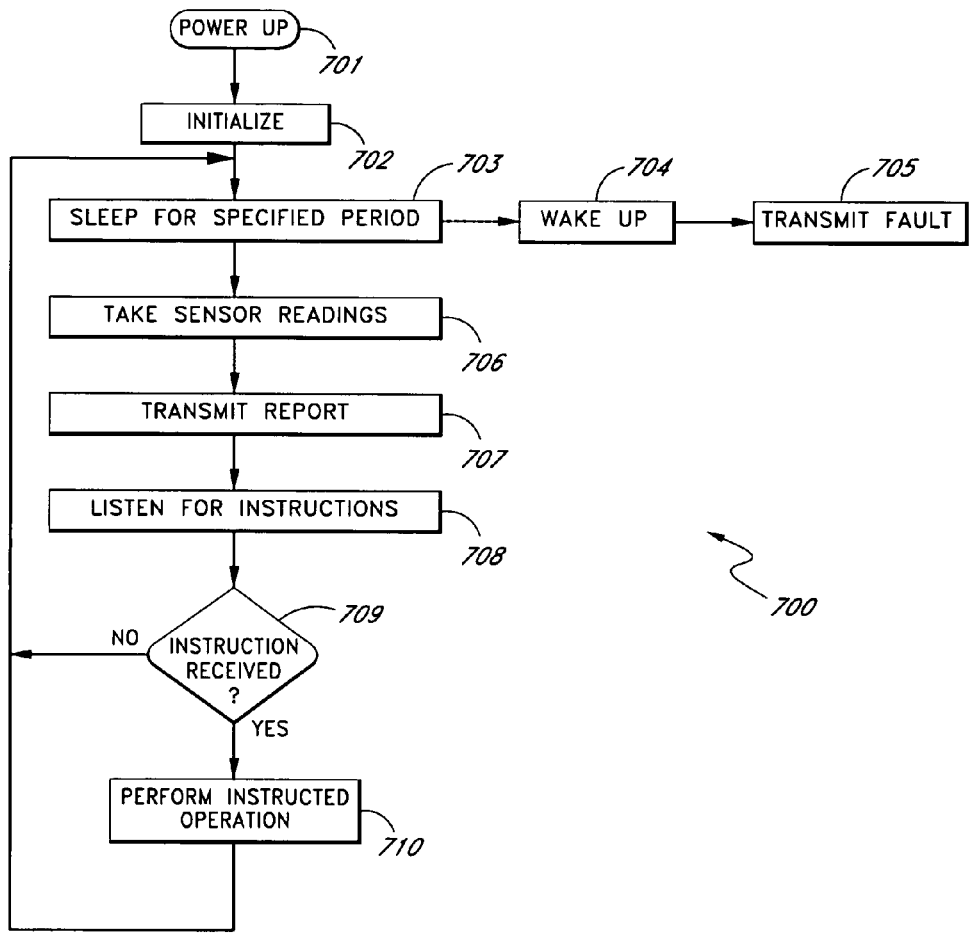
FIG. 7 is a flowchart showing operation of a sensor unit that provides periodic monitoring.

Relatively continuous monitoring, such as shown in FIG. 6, is appropriate for sensor units that sense relatively high-priority data (e.g., smoke, fire, carbon monoxide, flammable gas, etc.). By contrast, periodic monitoring can be used for sensors that sense relatively lower priority data (e.g., humidity, moisture, water usage, etc.). FIG. 7 is a flowchart showing one embodiment of operation of the sensor unit 102 wherein periodic monitoring is provided. In FIG. 7, a power up block 701 is followed by an initialization block 702. After initialization, the sensor unit 102 enters a low-power sleep mode. If a fault occurs during the sleep mode (e.g., the tamper sensor is activated), then the process enters a wake-up block 704 followed by a transmit fault block 705. If no fault occurs during the sleep period, then when the specified sleep period has expired, the process enters a block 706 where the sensor unit 102 takes a sensor reading from the sensor(s) 201. The sensor data is subsequently sent to the monitoring computer 113 in a report block 707. After reporting, the sensor unit 102 enters a listen block 708 where the sensor unit 102 listens for a relatively short period of time for instructions from monitoring computer 708. If an instruction is received, then the sensor unit 102 performs the instructions, otherwise, the process returns to the sleep block 703. In one embodiment, the sensor 201 and transceiver 203 are normally powered down. The controller 202 powers up the sensor 201 during execution of the block 706. The controller 202 powers up the transceiver during execution of the blocks 705, 707, and 708. The monitoring computer 113 can send instructions to the sensor unit 102 to change the sleep period used in block 703, the listen period used in block 708, etc.

In one embodiment, the sensor unit transmits sensor data until a handshaking-type acknowledgement is received. Thus, rather than sleep of no instructions or acknowledgements are received after transmission (e.g., after the decision block 613 or 709) the sensor unit 102 retransmits its data and waits for an acknowledgement. The sensor unit 102 continues to transmit data and wait for an acknowledgement until an acknowledgement is received. In one embodiment, the sensor unit accepts an acknowledgement from a repeater unit 111 and it then becomes the responsibility of the repeater unit 111 to make sure that the data is forwarded to the base unit 112. In one embodiment, the repeater unit 111 does not generate the acknowledgement, but rather forwards an acknowledgement from the base unit 112 to the sensor unit 102. The two-way communication ability of the sensor unit 102 provides the capability for the base unit 112 to control the operation of the sensor unit 102 and also provides the capability for robust handshaking-type communication between the sensor unit 102 and the base unit 112.

Regardless of the normal operating mode of the sensor unit 102 (e.g., using the Flowcharts of FIGS. 6, 7, or other modes) in one embodiment, the monitoring computer 113 can instruct the sensor unit 102 to operate in a relatively continuous mode where the sensor repeatedly takes sensor readings and transmits the readings to the monitoring computer 113. Such a mode would can be used, for example, when the sensor unit 102 (or a nearby sensor unit) has detected a potentially dangerous condition (e.g., smoke, rapid temperature rise, etc.)

Figure 8:
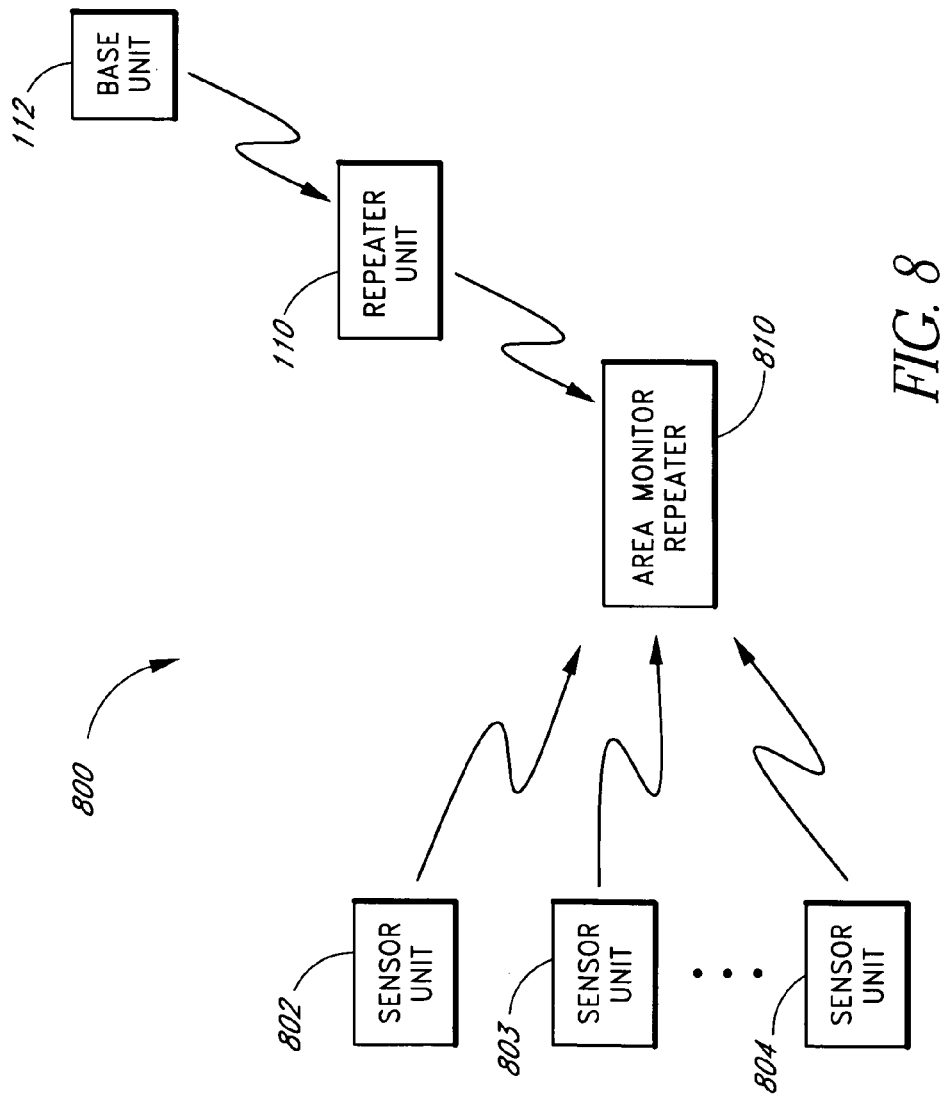
FIG. 8 shows a sensor system wherein relatively low-cost sensors provide sensor readings and/or status information to an area monitor that communicates with a base unit.

FIG. 8 shows a sensor system 800 wherein one or more relatively low-cost sensor units 802–804 provides sensor readings and/or status information to an area monitor unit 810 that communicates with the base unit 112 or with a repeater unit 110. The sensor units 802–804 can be configured as embodiments of the sensor unit 102 and/or as embodiments of the moisture sensor unit 1010. In one embodiment, the sensor units 802 and 804 are configured for one-way communication to transmit information to the area monitor 810. The moisture sensor unit 1010 can be configured as one embodiment of the sensor unit 102. The moisture sensor unit 1010 can be configured as shown in FIG. 2 with a transceiver 203 that can both transmit and receive, or the transceiver 203 can be configured for transmit-only operation. In one embodiment, the area monitor 810 is configured in a manner similar to the repeater unit 110.

In one embodiment, the area monitor 810 is configured to provide bi-directional communication with one or more sensor units 102. In one embodiment, the area monitor 810 is configured to receive one-way communication from one or more sensor units 802–804.

In one embodiment, the sensor unit 802 sends a message to the area monitor 810 whenever an anomalous sensor reading is detected (e.g., water is detected, smoke is detected, etc.). In one embodiment, the sensor unit 802 sends a stream of messages spaced at desired intervals (e.g., every few seconds) to the area monitor 810 whenever an anomalous sensor reading is detected. In one embodiment, the sensor unit 802 sends a status report (e.g., system health, battery power status, etc.) to the area monitor 810 at a desired regular interval (e.g., every hour, every day, every few hours, etc.). The area monitor forwards messages from the sensor system 800 to the monitoring system 113. In one embodiment, the monitoring system 113 and/or area monitor 810 can determine that the sensor unit 802 has failed based on status information received from the sensor unit 802 and/or based on a lack of status information from the sensor unit 802. The area monitor 810 expects to receive periodic status updates from the sensor 802, thus, the area monitor (and the central monitor 113) can assume that the sensor unit 802 has failed or been removed if such regular status updates are not received.

In one embodiment, the sensor unit 802 send actual sensor data to the area monitor 810 and the area monitor forwards such data to the central monitoring system 113 for analysis. Thus, unlike simple alarm systems that simply provide on/off-type sensors, the sensor units 802–804 and 102–106 provide actual sensor readings that can be analyzed by the monitoring system to determine or estimate the severity of a problem (e.g., the amount of smoke, the amount of water, the rate of increase in smoke, water, temperature, etc.).

In one embodiment, the monitoring system 113 maintains data received from the sensor units 802–804 and 102–106 to help in maintenance of the sensor system. In one embodiment, maintenance personnel are expected to test each sensor unit on a regular basis (e.g., semi-annually, annually, bi-annually, monthly, etc.) to make sure the sensor is working. Thus, for example, in one embodiment, the maintenance personnel are expected to expose each moisture sensor 1010 to water to test the operation of the sensor and to make sure that a "water-sensed" message is transmitted to the monitoring system 113. Similarly, the maintenance personnel can be tasked with exposing each smoke sensor to smoke. Thus, if the monitoring system database shows that a particular sensor unit has not reported a sensor event (e.g., water detected, smoke detected, etc.) in a period corresponding to the maintenance interval, the monitoring system 113 can report that the sensor unit has failed or that the sensor unit has not been tested according to the testing schedule. In this manner, supervisory personnel can monitor the actions of maintenance personnel by examining the database maintained by the system 113 to make sure that each sensor has been activated and tested according the desired maintenance schedule.

The database maintained by the monitoring system 113 can also be used to provide plots of sensor activations and to indicate possible trouble areas in a building or structure. Thus, for example, if a particular water sensor has been activated on a regular basis, the monitoring system 113 can indicate that a potential problem exists in the area monitored by that sensor and thus, alert the maintenance or supervisory personnel.

Excess moisture in a structure can cause severe problems such as rotting, growth of molds, mildew, and fungus, etc. (hereinafter referred to generically as fungus). In one embodiment, the sensor 201 includes a moisture sensor. In one embodiment, the monitoring system 100 detects conditions favorable for fungus (e.g., mold, mildew, fungus, etc.) growth by measuring moisture content of the building material at one or more locations of a building. In one embodiment, sensor system is used to detect moisture in building materials, such as, for example, drywall, wood, concrete, plaster, stucco, etc. In one embodiment, the sensor unit 102 includes a moisture sensor and one or more moisture probes coupled to the building material. The moisture probes are provided to the building material to allow the sensor unit 102 to detect and/or measure the presence of moisture in the material. Moisture in the building material is generally the result of a leak (e.g., plumbing leak, roof leak, stucco leak, etc.), invasion of ground water, trapped humidity, or condensation. In one embodiment, the severity of a moisture problem is ascertained by the sensor unit 102 (or the monitoring computer 113) by measuring (or estimating) the rate of rise in the moisture level and/or by measuring (or estimating) the size of a moist area, and/or by measuring (or estimating) the amount of moisture in the building material.

In one embodiment, the monitoring computer 113 compares moisture measurements taken from different sensor units in order to detect areas that have excess moisture. Thus, for example, the monitoring computer 113 can compare the moisture readings from a first sensor unit 102 in a first attic area, to a moisture reading from a second sensor unit 102 in a second area. For example, the monitoring computer can take moisture readings from a number of attic areas to establish a baseline moisture reading and then compare the specific moisture readings from various sensor units to determine if one or more of the units are measuring excess moisture. The monitoring computer 113 would flag areas of excess moisture for further investigation by maintenance personnel. In one embodiment, the monitoring computer 113 maintains a history of moisture readings for various sensor units and flags areas that show an unexpected increase in moisture for investigation by maintenance personnel.

The monitoring station 113 collects moisture readings from the first moisture sensor and the second moisture sensor and indicates conditions favorable for fungus growth by comparing the first moisture data and the second moisture data. In one embodiment, the monitoring station 113 establishes a baseline moisture by comparing moisture readings from a plurality of moisture sensors and indicates possible fungus growth conditions in the first building area when at least a portion of the first moisture data exceeds the baseline moisture by a specified amount. In one embodiment, the monitoring station 113 establishes a baseline moisture by comparing moisture readings from a plurality of moisture sensors and indicates possible fimgus growth conditions in the first building area when at least a portion of the first moisture data exceeds the baseline moisture by a specified percentage.

In one embodiment, the monitoring station 113 establishes a baseline moisture history by comparing moisture readings from a plurality of moisture sensors and indicates possible fungus growth conditions in the first building area when at least a portion of the first moisture data exceeds the baseline moisture history by a specified amount over a specified period of time. In one embodiment, the monitoring station 113 establishes a baseline moisture history by comparing moisture readings from a plurality of moisture sensors over a period of time and indicates possible fungus growth conditions in the first building area when at least a portion of the first moisture data exceeds the baseline moisture by a specified percentage of a specified period of time.

In one embodiment, the sensor unit 102 transmits moisture data when it determines that the moisture data fails a threshold test. In one embodiment, the moisture threshold for the threshold test is provided to the sensor unit 102 by the monitoring station 113. In one embodiment, the moisture threshold for the threshold test is computed by the monitoring station from a baseline moisture established in the monitoring station. In one embodiment, the baseline moisture is computed at least in part as an average of moisture readings from a number of moisture sensors. In one embodiment, the baseline moisture is computed at least in part as a time average of moisture readings from a number of moisture sensors. In one embodiment, the baseline moisture is computed at least in part as a time average of moisture readings from a moisture sensor. In one embodiment, the baseline moisture is computed at least in part as the lesser of a maximum moisture reading an average of a number of moisture readings.

In one embodiment, the sensor unit 102 reports moisture readings in response to a query by the monitoring station 113. In one embodiment, the sensor unit 102 reports moisture readings at regular intervals. In one embodiment, a moisture interval is provided to the sensor unit 102 by the monitoring station 113.

In one embodiment, the calculation of conditions for fungus growth is comparing moisture readings from one or more moisture sensors to the baseline (or reference) moisture. In one embodiment, the comparison is based on comparing the moisture readings to a percentage (e.g., typically a percentage greater than 100%) of the baseline value. In one embodiment, the comparison is based on comparing the moisture readings to a specified delta value above the reference moisture. In one embodiment, the calculation of likelihood of conditions for fungus growth is based on a time history of moisture readings, such that the longer the favorable conditions exist, the greater the likelihood of fungus growth. In one embodiment, relatively high moisture readings over a period of time indicate a higher likelihood of fungus growth than relatively high moisture readings for short periods of time. In one embodiment, a relatively sudden increase in moisture as compared to a baseline or reference moisture is reported by the monitoring station 113 as a possibility of a water leak. If the relatively high moisture reading continues over time then the relatively high moisture is reported by the monitoring station 113 as possibly being a water leak and/or an area likely to have fungus growth or water damage.

Temperatures relatively more favorable to fungus growth increase the likelihood of fungus growth. In one embodiment, temperature measurements from the building areas are also used in the fungus grown-likelihood calculations. In one embodiment, a threshold value for likelihood of fungus growth is computed at least in part as a function of temperature, such that temperatures relatively more favorable to fungus growth result in a relatively lower threshold than temperatures relatively less favorable for fungus growth. In one embodiment, the calculation of a likelihood of fungus growth depends at least in part on temperature such that temperatures relatively more favorable to fungus growth indicate a relatively higher likelihood of fungus growth than temperatures relatively less favorable for fungus growth. Thus, in one embodiment, a maximum moisture and/or minimum threshold above a reference moisture is relatively lower for temperature more favorable to fungus growth than the maximum moisture and/or minimum threshold above a reference moisture for temperatures relatively less favorable to fungus growth.

In one embodiment, a water flow sensor is provided to the sensor unit 102. The sensor unit 102 obtains water flow data from the water flow sensor and provides the water flow data to the monitoring computer 113. The monitoring computer 113 can then calculate water usage. Additionally, the monitoring computer can watch for moisture, by, for example, looking for water flow when there should be little or no flow. Thus, for example, if the monitoring computer detects water usage throughout the night, the monitoring computer can raise an alert indicating that a possible water leak has occurred.

In one embodiment, a rain sensor is provided to the monitoring computer 113 and one or more water shutoff valves are provided to the monitoring computer 113 to allow the monitoring computer 113 to shut off the water supply to one or more areas of a building. If one or more moisture sensors report a relatively rapid rise in moisture levels when it is not raining, then the monitoring computer can shut off the water supply to the affected area of the buildings (on the assumption that the moisture is coming from a plumbing leak).

Figure 9:
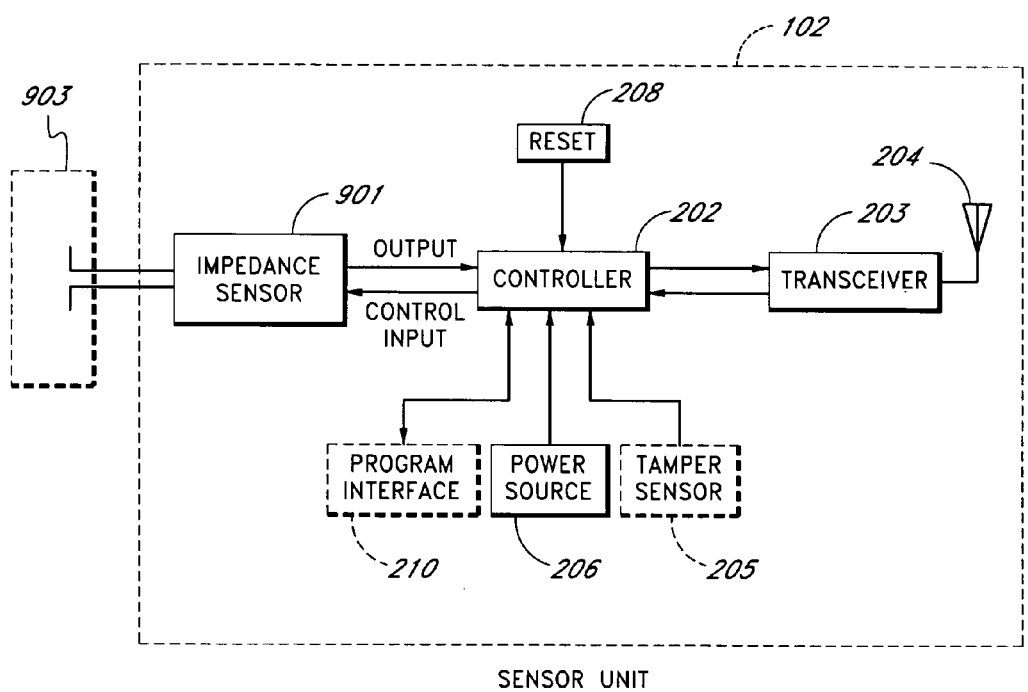
FIG. 9 shows a moisture sensor that includes an impedance sensor provided to one or more impedance probes.

FIG. 9 shows a moisture sensor unit 902 that includes an impedance sensor 901 provided to an impedance probe 903. The sensor unit 902 is one embodiment of the sensor units 102 or 802 wherein the sensor 201 is configured as an impedance sensor 901. The impedance sensor 901 measures the impedance of the probe 903. In one embodiment, the impedance sensor 901 measures a resistance of the probe 903. In one embodiment, the impedance sensor 901 measures an AC resistance of the probe 903. In one embodiment, the impedance sensor 901 measures an AC reactance of the probe 903. The impedance sensor 901 receives a control input from the controller 202 and provides output data to the controller 202.

The impedance of most building materials varies as the moisture content of the building material changes. Typically, most building materials (e.g., concrete, drywall, plaster, wood, etc.) have a relatively high impedance when dry, and the impedance goes down as the moisture level increases. Thus, one convenient way to measure the moisture content of many building materials is to measure the impedance of a probe provided to the building material.

If only the DC resistance is desired, then the probe is provided in direct electrical contact with the building material. If the AC impedance is desired, then the probe can be provided in direct electrical contact with the building material or the probe can be capacitively coupled to the building material through a dielectric.

The probe is typically provided to the building material when the material is dry. The impedance sensor measures the impedance of the probe at specified intervals. In one embodiment, a change in the impedance is reported by the sensor unit 902 to the monitoring system 113 as a possible increase in moisture content.

In one embodiment, the measured impedance data, the electrical characteristics of the probe, and the type of building material to which the probe is attached are provided to the monitoring system 113 to allow the monitoring system 113 to compute a moisture content value from the impedance data.

In one embodiment, a threshold value (as described above) is provided to the sensor unit 902 and the sensor unit reports impedance data when the measured impedance values cross the threshold. In one embodiment, the threshold is an upper threshold, and the impedance data is reported when the measured impedance values exceed the threshold. In one embodiment, the threshold is a lower threshold, and the impedance data is reported when the measured impedance values fall below the threshold. In one embodiment, the threshold is configured as an inner range. In one embodiment, the threshold is configured as an outer range. In one embodiment, a threshold is provided for the magnitude of the impedance. In one embodiment, a threshold is provided for the real part of the impedance (e.g., the resistance). In one embodiment, a threshold is provided for the imaginary part of the impedance (e.g., the reactance).

For example, drywall (gypsum) and/or plaster have a relatively high impedance with dry and the impedance drops as the moisture content increases. In one embodiment, the sensor unit 902 reports impedance data to the monitoring system 113 whenever the impedance measured by the impedance sensor 1002 drops by a specified amount. In one embodiment, the sensor unit 902 reports impedance data to the monitoring system 113 whenever the impedance measured by the impedance sensor 1002 drops by a specified amount, where the specified amount is specified according to the type of material the probe 1001 is attached to.

In one embodiment, the sensor unit 902 reports impedance data to the monitoring system 113 at specified intervals and whenever the impedance measured by the impedance sensor 1002 drops by a specified amount. The monitoring system 113 establishes a "dry" impedance value by recording the highest impedance reported by the sensor unit 902.

Figure 10:
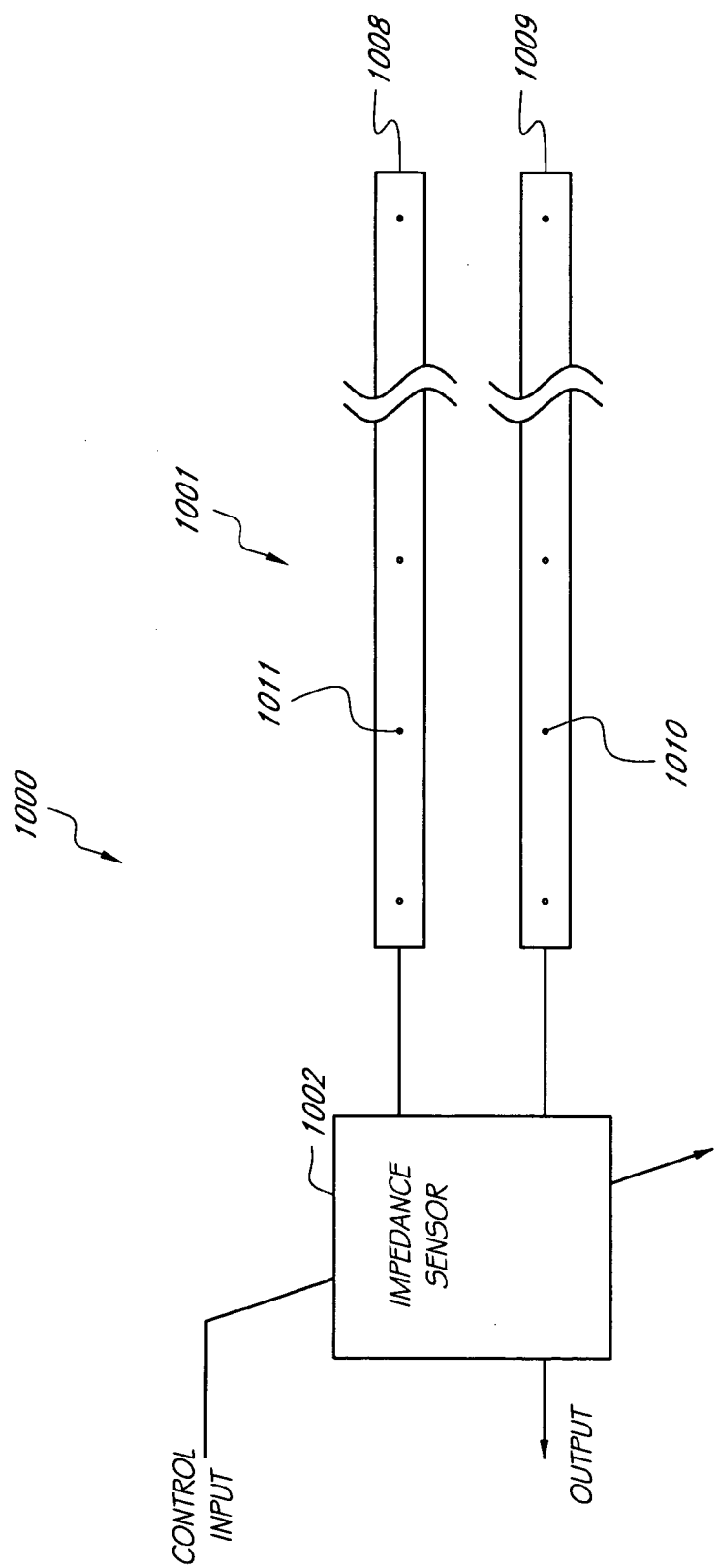
FIG. 10 shows the impedance sensor from FIG. 9 provided to an impedance probe configured as a pair of conductive strips.

FIG. 10 shows an impedance sensor 1002 (corresponding to the impedance sensor 902 from FIG. 9) provided to an impedance probe 1001 configured as a pair of conductive strips 1008, 1009. Optionally, in one embodiment, two or more pins 1010, 1011 are provided to the conductive strips 1008, 1009. In one embodiment, when the probe 1001 is installed, the pins 1010, 1011 are inserted into the building material in order to provide better electrical contact with the building material. The pins 1010, 1011 can be configured as sharp pins attached to the strips 1008, 1009, nails and/or staples driven through the strips 1008, 1009, etc.

In response to the control input from the controller 202, the impedance sensor measures the impedance of the probe 1001. In one embodiment, the expected impedance values for wet and moist conditions are determined from the type of building material and the characteristics of the probe 1001 (e.g., length, number of pins, etc.).

Figure 11:
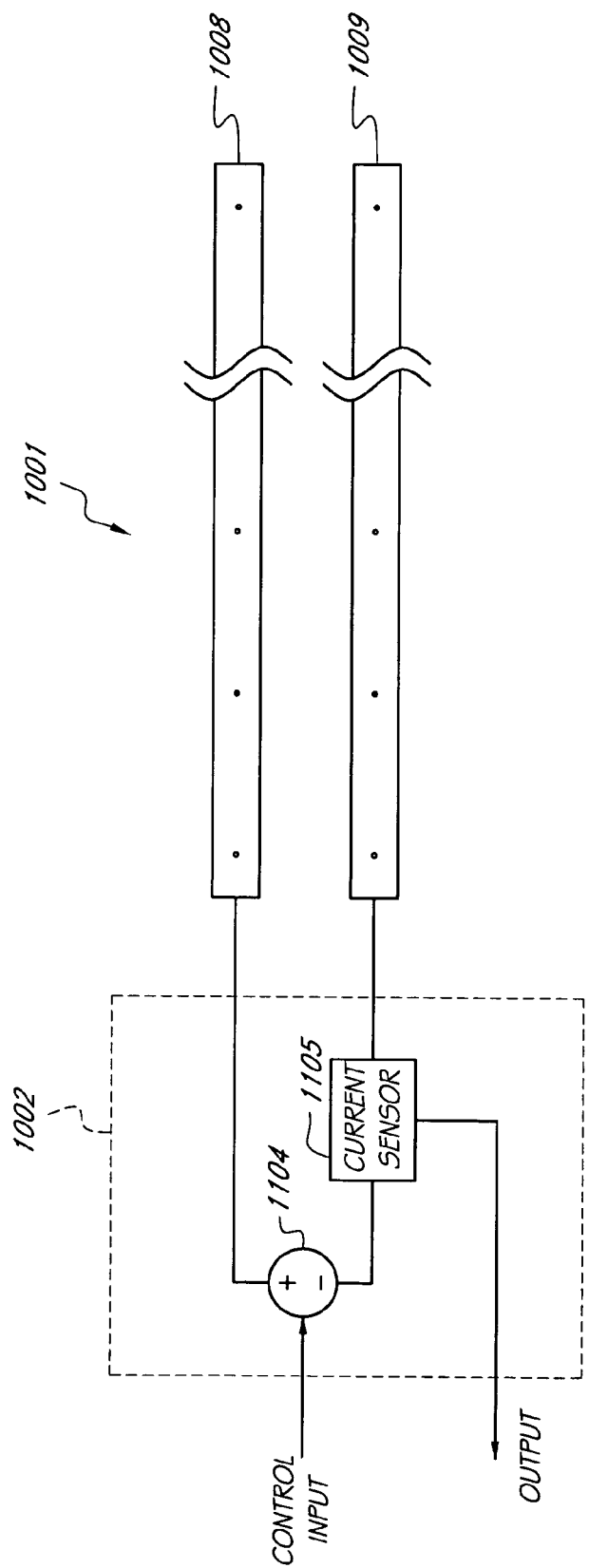
FIG. 11 is a schematic of an impedance sensor configured to measure impedance by using a voltage source and a current sensor.

FIG. 11 is a schematic of an impedance sensor 1002 configured to measure impedance by using a voltage source 1904 and a current sensor 1105. The voltage source provides a voltage between the conductors 1008, 1009, and the current sensor 1105 then measures the current through the probe. The impedance is then calculated by using Ohm's law. In one embodiment, the controller 202 controls the voltage produced by the voltage source 1104. In one embodiment, the voltage source 1104 is a DC source. In one embodiment, the voltage source 1104 is an AC source. In one embodiment, the controller 202 controls the frequency and/or phase of the voltage source 1104. In one embodiment, the current sensor 1105 measures magnitude of the current through the current through the probe 1001. In one embodiment, the current sensor 1105 measures magnitude and phase of the current through the current through the probe 1001.

Figure 12:
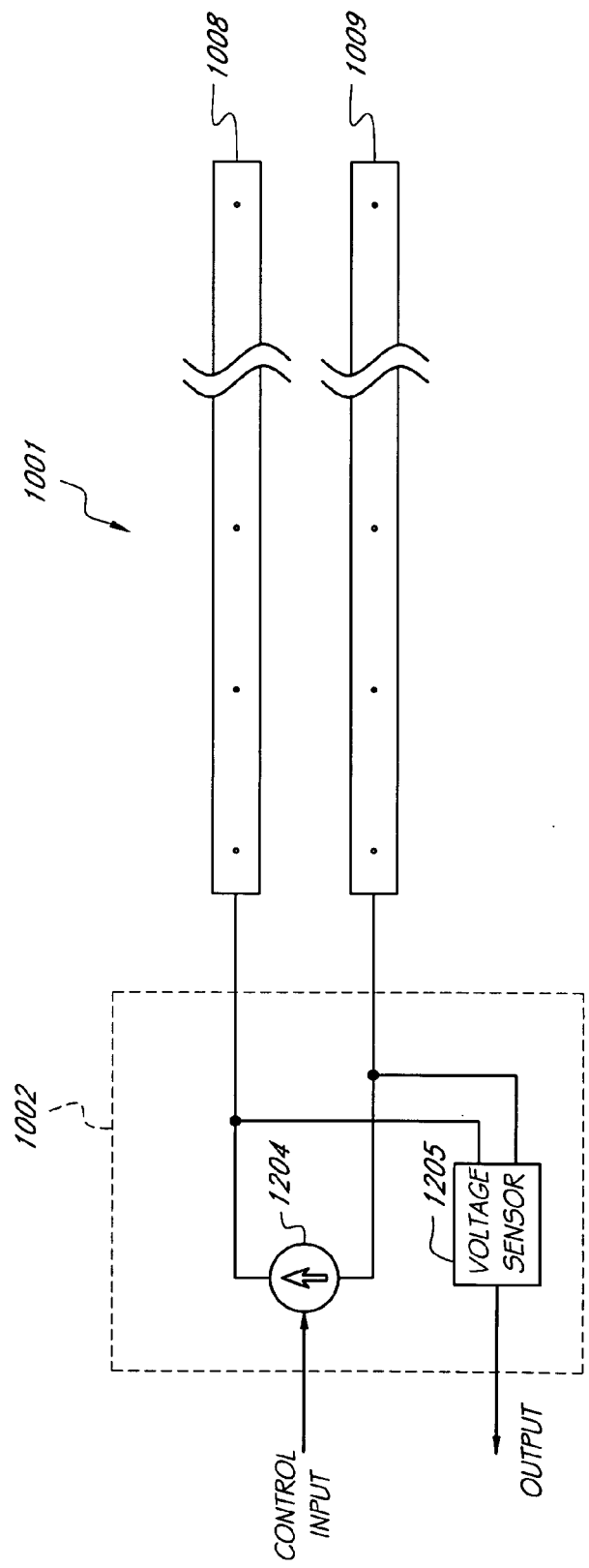
FIG. 12 is a schematic of an impedance sensor configured to measure impedance by using a current source and a voltage sensor.

FIG. 12 is a schematic of an impedance sensor 1002 configured to measure impedance by using a current source 1204 and a voltage sensor 1205. The current source 1204 provides a current through the conductors 1008, 1009, and the voltage sensor 1205 then measures the voltage across the probe 1001. The impedance is then calculated by using Ohm's law. In one embodiment, the controller 202 controls the current produced by the current source 1204. In one embodiment, the current source 1204 is a DC source. In one embodiment, the current source 1204 is an AC source. In one embodiment, the controller 202 controls the frequency and/or phase of the current source 1204. In one embodiment, the voltage sensor 1205 measures magnitude of the current through the voltage across the probe 1001. In one embodiment, the current sensor 1205 measures magnitude and phase of the voltage across the current through the probe 1001.

Figure 13:
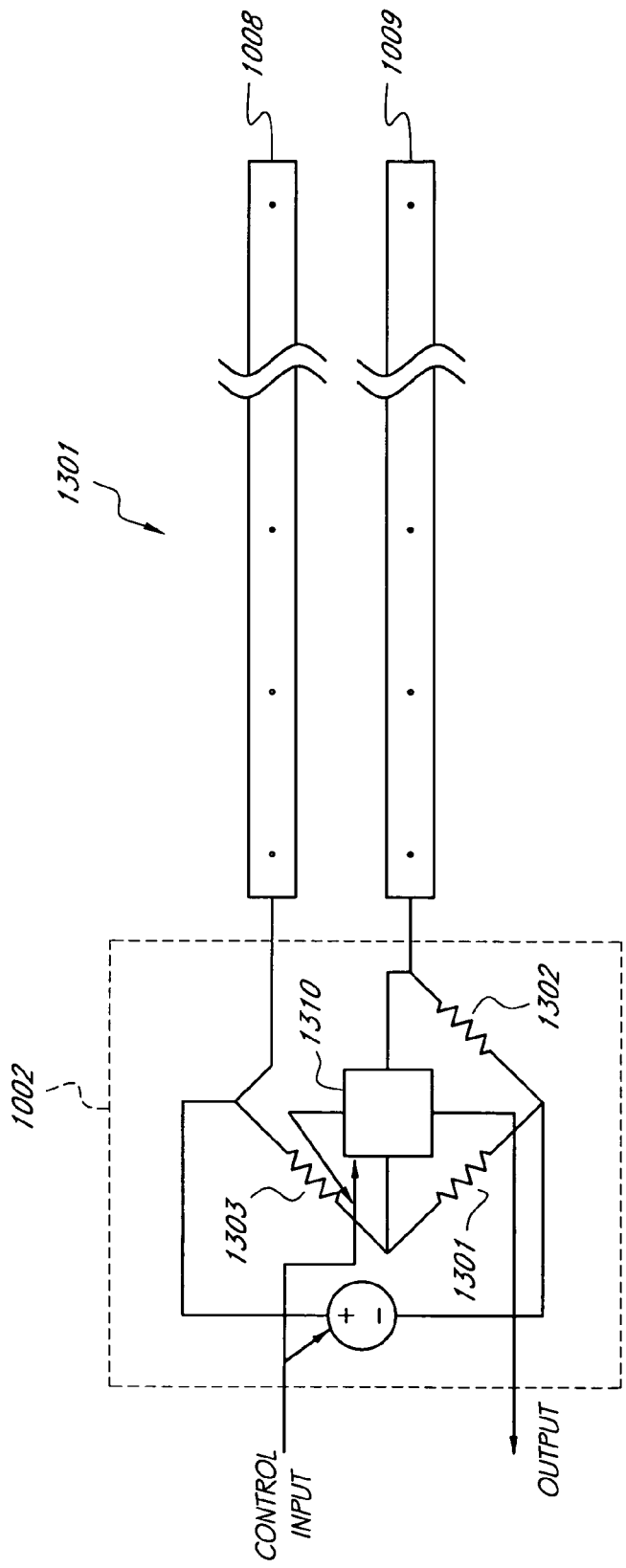
FIG. 13 is a schematic of an impedance sensor configured to measure impedance using a bridge.

FIG. 13 is a schematic of an impedance sensor 1002 configured to measure impedance using an impedance bridge that includes impedances 1301–1303 in three legs of the bridge, and the probe is provided to the fourth leg of the bridge. The control input is provided to a voltage source that drives the bridge and to a module 1310 that measures the impedance across the bridge. In one embodiment, the impedance 1303 is fixed. In one embodiment, the impedance 1303 is varied by the control module 1310. In one embodiment, the impedance 1303 is fixed. In one embodiment, the impedance 1303 is varied by the control module 1310 in response to the control input. The impedance of across the probe 1001 is then calculated as known in the art by using the known impedances 1301–1303 and the voltage across the bridge.

Figure 14:
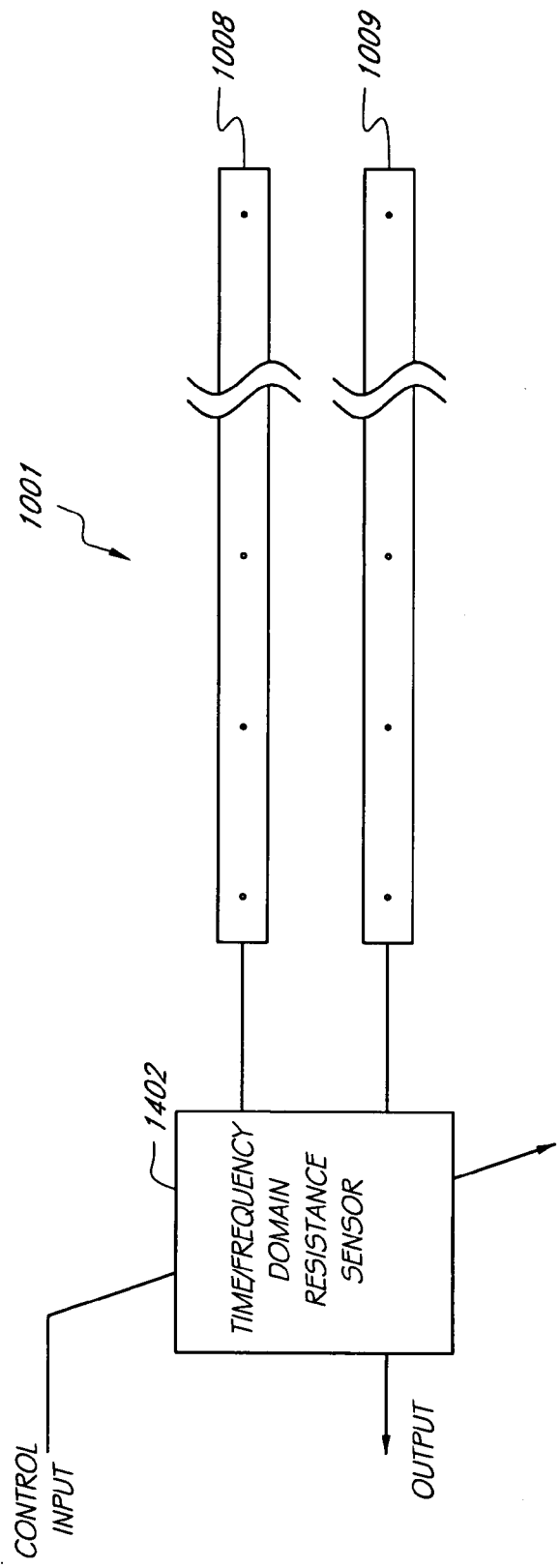
FIG. 14 shows a moisture sensor that includes a time/frequency domain impedance sensor provided to an impedance probe.

FIG. 14 shows a moisture sensor that includes a time/frequency domain impedance sensor 1402 provided to the impedance probe 1001. In one embodiment, the time-frequency domain impedance sensor 1402 uses time-domain and/or frequency domain measurement techniques to measure the impedance properties along the impedance probe 1001. In one embodiment, the time-frequency domain impedance sensor 1402 uses time-domain measurement techniques to measure the impedance properties along the impedance probe 1001 by sending a relatively short pulse of energy along the impedance probe 1001 and measuring the reflections of the energy pulse. In one embodiment, the time-frequency domain impedance sensor 1402 is configured as a time-domain reflectometer. In one embodiment, the time-frequency domain impedance sensor 1402 measures the impedance of the impedance probe 1001 at various frequencies, and then uses Fourier transform techniques to transform the measurements from the frequency domain into the time domain. In one embodiment, the time-domain data are used to identify regions along the impedance probe 1001 that are relatively more moist.

Figure 15:
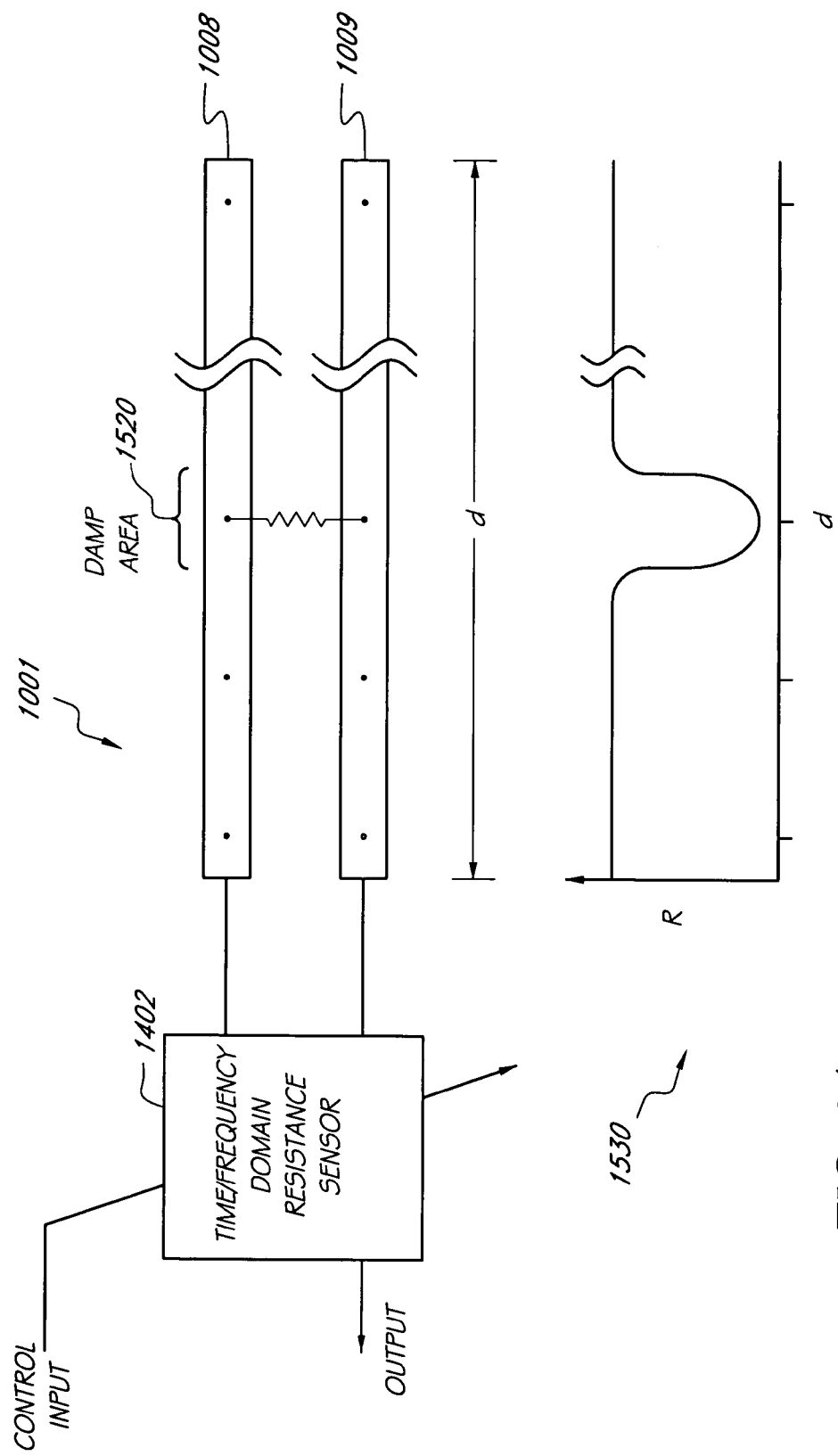
FIG. 15 is a plot showing an example output of the time-frequency domain impedance sensor when a relatively small clamp area is detected.

FIG. 15 is a plot showing an example output of the time-frequency domain impedance sensor 1402 when a relatively small damp area 1502 is detected. When the impedance probe 1001 is provided to a building material that has a smaller impedance when moist, the impedance of the impedance probe 1001 is smaller in the region 1502 and thus the impedance probe 1001 produces a reflection corresponding to the region 1502. By way of example, FIG. 15 includes a graph 1530 showing the reduced resistance corresponding to the region 1502.

Figure 16:
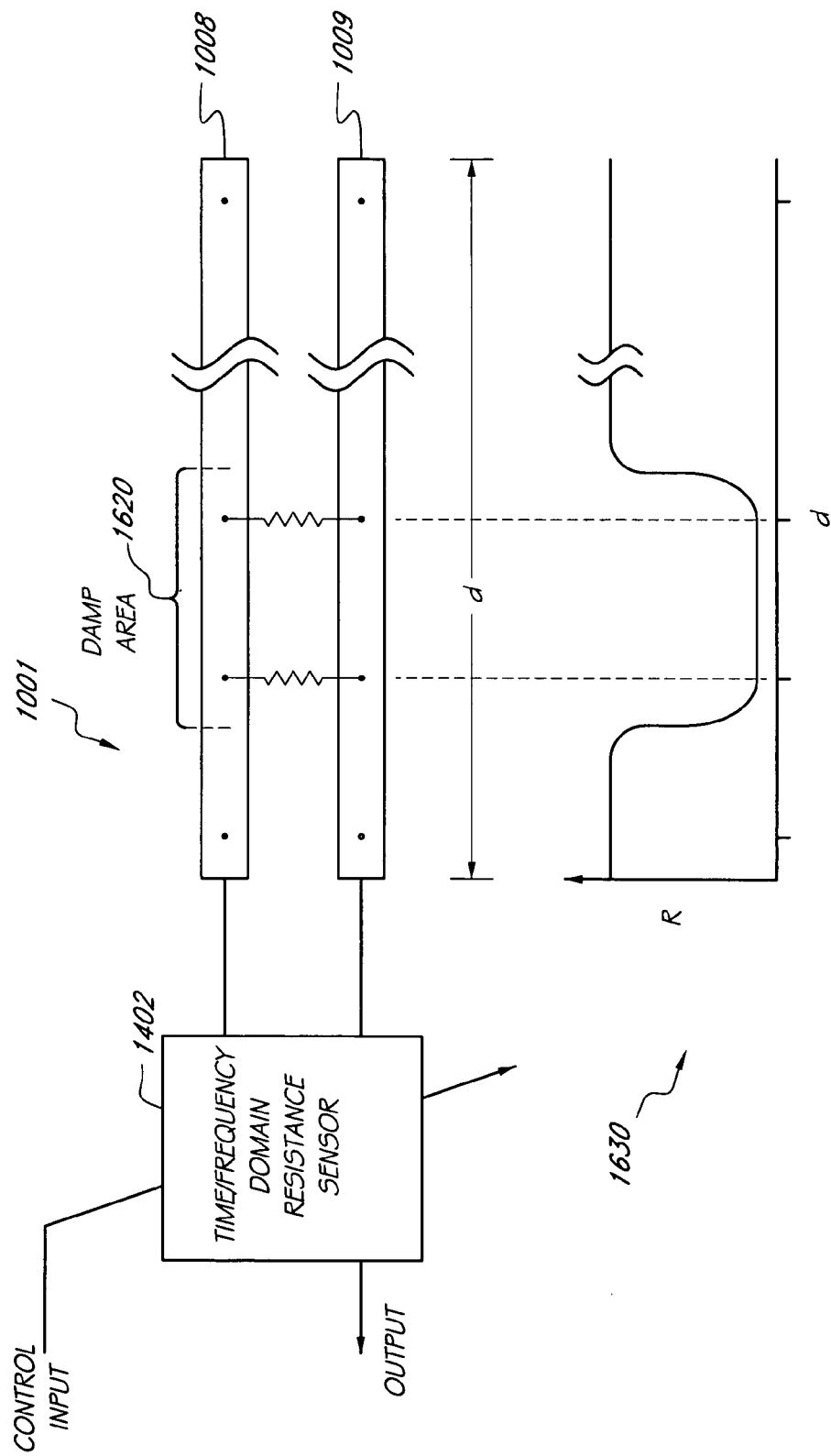
FIG. 16 is a plot showing an example output of the time-frequency domain impedance sensor when a larger damp area is detected.

FIG. 16 is a plot showing an example output of the time-frequency domain impedance sensor 1402 when a relatively larger damp area 1602 is detected. When the impedance probe 1001 is provided to a building material that has a smaller impedance when moist, the impedance of the impedance probe 1001 is smaller in the region 1502 and thus, the impedance probe 1001 produces a reflection corresponding to the region 1001. By way of example, FIG. 16 includes a graph 1630 showing the reduced resistance corresponding to the region 1502. Comparison of the graphs 1530 and 1630 shows that the time/frequency domain impedance sensor 1402 can be used to provide an indication of the location, size, and severity of the moist area. The location of the moist area is indicated by the location of the moist area along the impedance probe 1001 (where time can be converted into a distance along the probe according to the speed of propagation of an electrical signal along the probe). The size of the moist area is indicated by the size of the region of lower impedance along the impedance probe 1001. The amount of moisture in the building material at different points along the impedance probe 1001 is computed from the measured impedance at various points along the impedance probe 1001 and knowledge of the properties of the building material provided to the impedance probe.

In one embodiment, the time/frequency impedance sensor 1402 is configured according to the schematics shown in FIGS. 11–13 where the respective sources (voltage and/or current sources) are configured as AC (Alternating Current) sources or sources that produce a time-domain and/or frequency-domain waveform.

Figure 17:
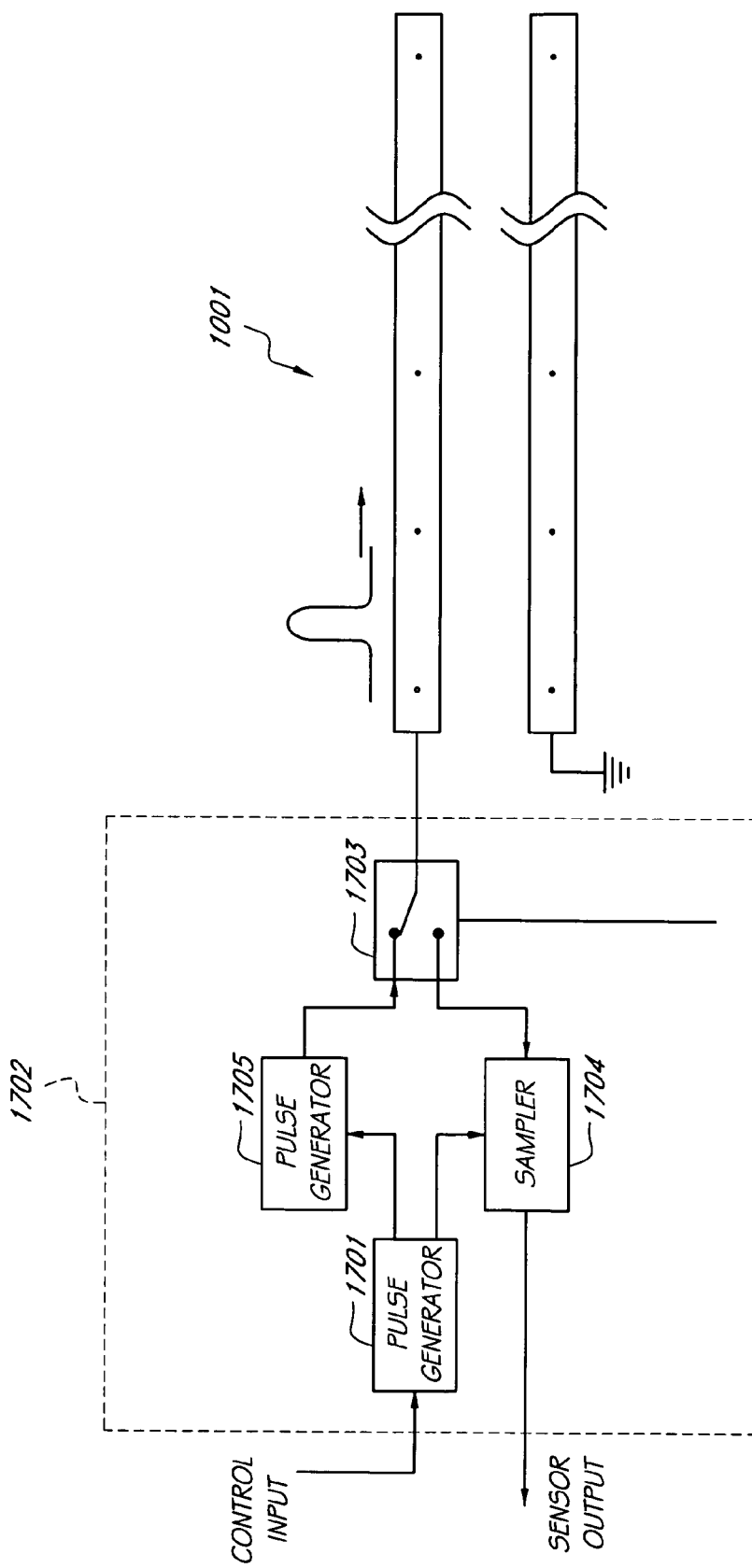
FIG. 17 is a schematic of one embodiment of a time-domain impedance sensor.

FIG. 17 is a schematic of one embodiment of the time/frequency domain impedance sensor 1402 configured as a pulse reflectometer having a pulse generator 1705, a diplexer switch 1703, and a sampler 1704. A timing generator 1701 is controlled by the control input and provides control outputs to the pulse generator 1705, the diplexer switch 1703, and the sampler 1704. The diplexer switch 1703 is typically an electronic switch configured using solid-state electronic elements to provide high speed and high reliability.

In a transmit mode, the timing generator places the diplexer switch 1703 in a "transmit position" (as shown), and instructs the pulse generator 1705 to provide a pulse of relatively-short time duration (e.g., implses, chirps, frequency pulses, etc) to the diplexer switch 1703. The diplexer switch 1703 provides the pulse to the impedance probe 1001. The timing generator then switches the diplexer switch 1703 to a "receive position" wherein when return pulse (or pulses) from the impedance probe 1001 are provided to the sampler 1704. The sampler 1704. The sampler provides sampled data from the impedance probe 1001 to the controller 202.

In one embodiment, the moisture sensor unit 902 is configured as an adjustable-threshold moisture sensor that computes a threshold level. In one embodiment, the threshold is computed as an average of a number of sensor measurements. In one embodiment, the average value is a relatively long-term average. In one embodiment, the average is a time-weighted average wherein recent sensor readings used in the averaging process are weighted differently than less recent sensor readings. In one embodiment, more recent sensor readings are weighted relatively more heavily than less recent sensor readings. In one embodiment, more recent sensor readings are weighted relatively less heavily than less recent sensor readings. The average is used to set the threshold level. When the moisture sensor readings rise above the threshold level, the moisture sensor indicates a notice condition. In one embodiment, the moisture sensor indicates a notice condition when the moisture sensor reading rises above the threshold value for a specified period of time. In one embodiment, the moisture sensor indicates a notice condition when a statistical number of sensor readings (e.g., 3 of 2, 5 of 3, 10 of 7, etc.) are above the threshold level. In one embodiment, the moisture sensor unit 902 indicates various levels of alarm (e.g., warning, alert, alarm) based on how far above the threshold the moisture sensor reading has risen.

In one embodiment, the moisture sensor unit 902 computes the notice level according to how far the moisture sensor readings have risen above the threshold and how rapidly the moisture sensor readings have risen or how long the moisture reading have been elevated. A relatively fast rate of rise may be indicative of a relatively serious leak and/or a relatively large volume of water that could lead to water damage. An area that has been moist (even slightly moist) for a period of time may be indicative of long-term damage due to molds, fungus, rotting, etc. For example, for purposes of explanation, the level of readings and the rate of rise can be quantified as low, medium, and high. The combination of sensor reading level and rate of rise then can be show as a table, as show in Table 1. Tables 1 and 2 provide examples and is provided by way of explanation, not limitation.

TABLE 1

| | Sensor Reading Level (as compared to the threshold) | | | |
|---|---|---|---|---|
| Rate of Rise | High | Warning | Alarm | Alarm |
| | Medium | Notice | Warning | Alarm |
| | Low | Notice | Warning | Alarm |
| | | Low | Medium | High |

TABLE 2

| | Sensor Reading Level (as compared to the threshold) | | | |
|---|---|---|---|---|
| Length of Time | Long | Alarm | Alarm | Alarm |
| | Medium | Warning | Warning | Alarm |
| | Short | Notice | Warning | Alarm |
| | | Low | Medium | High |

One of ordinary skill in the art will recognize that the notice level N can be expressed as an equation $N=f(l, v, r, t)$, where l is the threshold level, v is the moisture sensor reading, r is the rate of rise, and t is the length of time of the moisture sensor reading. In embodiments where the size of the moist area can be measured (as described, for example, in connection with FIGS. 13–17), then the size of the moist area can also be included in the above equation and/or in the above tables. In one embodiment, the moisture sensor reading v and/or the rate of rise r are lowpass filtered in order to reduce the effects of noise in the moisture sensor readings. In one embodiment, the threshold is computed by lowpass filtering the moisture sensor readings v using a filter with a relatively low cutoff frequency. A filter with a relatively low cutoff frequency produces a relatively long-term averaging effect. In one embodiment, separate thresholds are computed for the moisture sensor reading and for the rate of rise.

In one embodiment, a calibration procedure period is provided when the moisture sensor unit 902 is powered up. During the calibration period, the moisture sensor data values from the moisture sensor 201 are used to compute the threshold value, but the moisture sensor does not compute notices, warnings, alarms, etc., until the calibration period is complete. In one embodiment, the moisture sensor unit 902 uses a fixed (e.g., pre-programmed) threshold value to compute notices, warnings, and alarms during the calibration period and then uses the adjustable threshold value once the calibration period has ended.

In one embodiment, the moisture sensor unit 902 determines that a failure of the moisture sensor 201 has occurred when the adjustable threshold value exceeds a maximum adjustable threshold value. In one embodiment, the moisture sensor unit 902 determines that a failure of the moisture sensor 201 has occurred when the adjustable threshold value falls below a minimum adjustable threshold value. The moisture sensor unit 902 can report such failure of the moisture sensor 201 to the base unit 112.

In one embodiment, the moisture sensor unit 902 obtains a number of sensor data readings from the moisture sensor 201 and computes the threshold value as a weighted average using a weight vector. The weight vector weights some sensor data readings relatively more than other sensor data readings.

In one embodiment, the moisture sensor unit 902 obtains a number of sensor data readings from the moisture sensor unit 201 and filters the moisture sensor data readings and calculates the threshold value from the filtered sensor data readings. In one embodiment, the moisture sensor unit applies a lowpass filter. In one embodiment, the moisture sensor unit 201 uses a Kalman filter to remove unwanted components from the moisture sensor data readings. In one embodiment, the moisture sensor unit 201 discards sensor data readings that are "outliers" (e.g., too far above or too far below a normative value). In this manner, the moisture sensor unit 902 can compute the threshold value even in the presence of noisy sensor data.

In one embodiment, the moisture sensor unit 902 indicates a notice condition (e.g., alert, warning, alarm) when the threshold value changes too rapidly. In one embodiment, the moisture sensor unit 902 indicates a notice condition (e.g., alert, warning, alarm) when the threshold value exceeds a specified maximum value. In one embodiment, the moisture sensor unit 902 indicates a notice condition (e.g., alert, warning, alarm) when the threshold value falls below a specified minimum value.

In one embodiment, the moisture sensor unit 902 adjusts one or more operating parameters of the moisture sensor 201 according the threshold value. Thus, for example, in the example of a moisture sensor, the moisture sensor unit 201 can adjust the voltage (or current) provided to the moisture probe.

Figure 18:
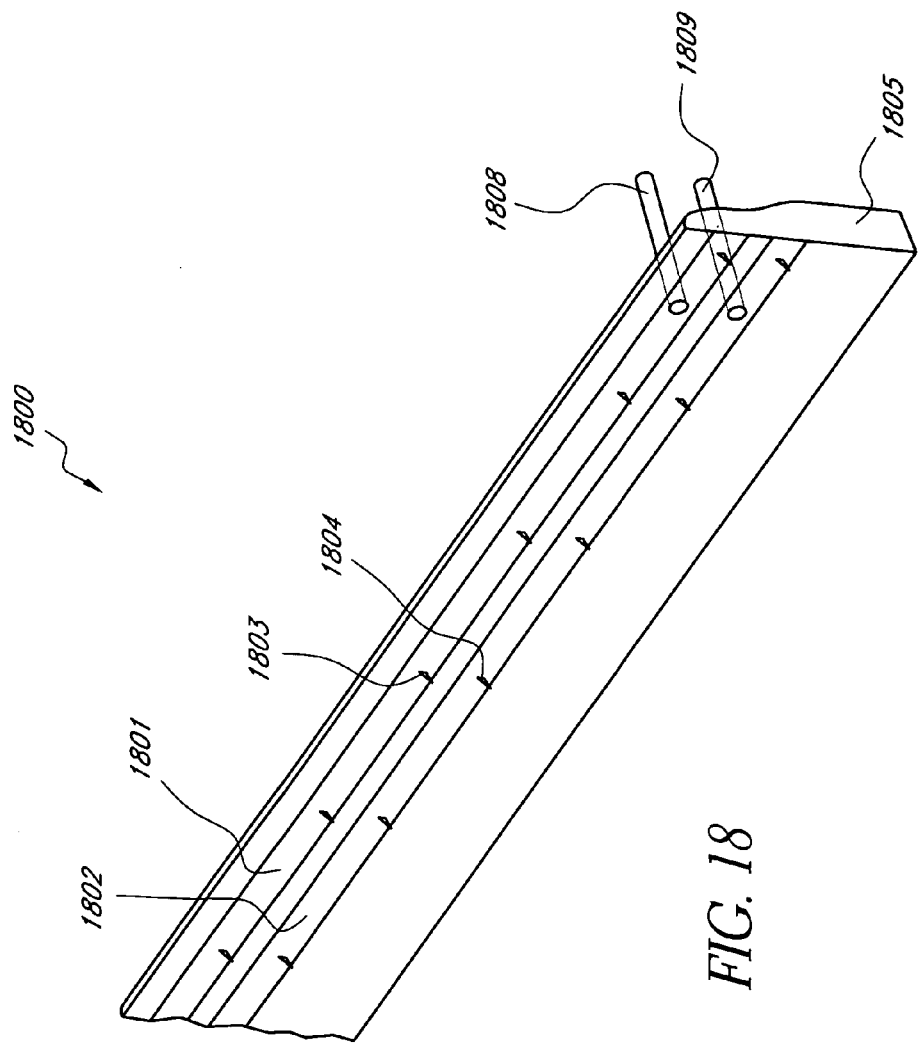
FIG. 18 is a rear view showing the impedance sensor provided to a molding.

FIG. 18 is a rear view showing one embodiment of the impedance probe 1001 configured as a molding system 1800. The molding system 1800 includes linear conductors 1801 and 1802 provided substantially along the length of a molding 1805. The molding 1805 can be configured as a typical decorative molding, such as, for example, a baseboard molding, door-jamb molding, crown molding, wainscot molding, etc. In one embodiment, the conductors 1801, 1802 are relatively smooth and configured to be capacitively coupled to a building material. In one capacitive coupling embodiment, the conductors are covered by a relatively thin layer of dielectric. In one embodiment, a plurality of sharp pins (e.g., pins 1803, 1804) are provide to electrically connect the conductors 1801, 1802 pierce into a wall or other building structure when the molding 1805 is attached to the wall (or structure). In one embodiment, the conductors 1801, 1802 and the optional pins (e.g., the pins 1803, 1804) are provided to the molding 1805 during manufacture. As with conventional molding, moldings according to the molding system 1800 are purchased, cut to length, and attached to a building by nails, glue, staples, screws, etc.

Figure 19:
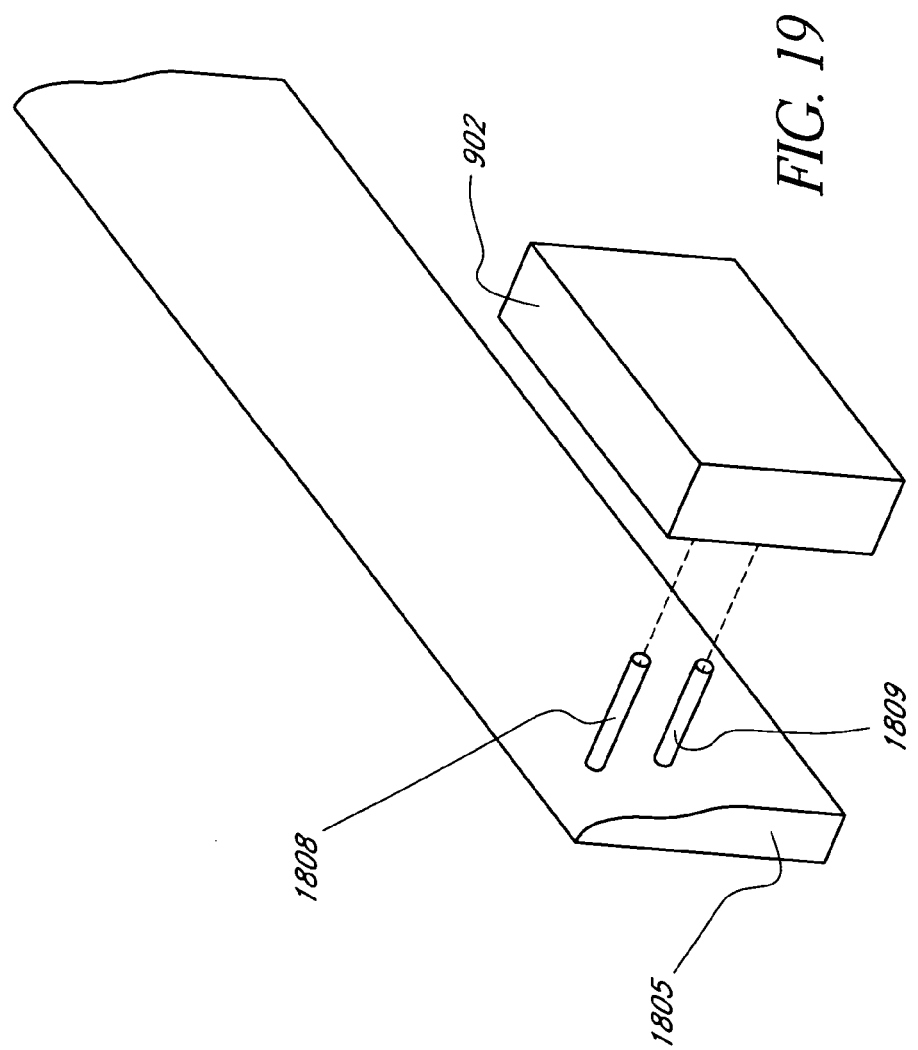
FIG. 19 is a front view of the molding from FIG. 9 showing one method connecting the sensor unit 902 to the impedance probe.

In one embodiment, connector pins 1808 and 1809 are provided to the conductors 1801 and 1802 respectively. The optional connector pins 1808, 1809 extend through to the front of the molding 1805 to provide electrical connection to sensor unit 802 provided to the front of the molding 1805, as shown in FIG. 19.

Figure 20:
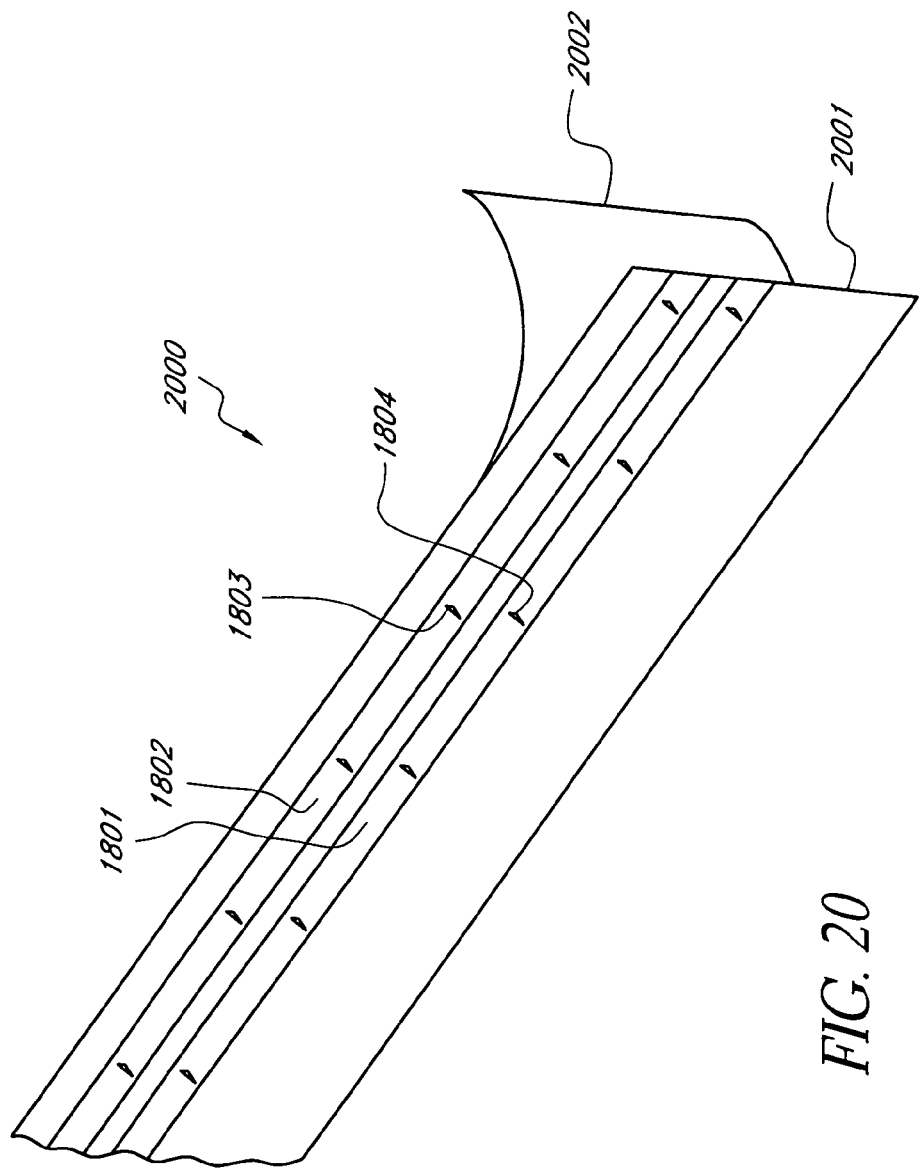
FIG. 20 shows an impedance probe configured for peel-and-stick application to a molding.

FIG. 20 shows the impedance probe 1001 configured as a relatively flexible tape 2000. In the tape 2000, the linear conductors 1801 and 1802 are provided to a dielectric substrate 2001 (e.g., plastic, mylar, nylon, etc.). In one embodiment, the conductors 1801, 1802 are relatively smooth and configured to be capacitively coupled to a building material. In one capacitive coupling embodiment, the conductors are covered by a relatively thin layer of dielectric. In one embodiment, the tape 2000 is attached to the desired building material by an adhesive. In one embodiment, the tape 2000 is attached to the desired building material by a plurality of staples (or nails) driven through the conductors 1801 and 1802 so as to provide electrical connection between the conductors and the building material.

In one embodiment, a plurality of sharp pins (e.g., pins 1803, 1804) are provide to electrically connect the conductors 1801, 1802 pierce into a wall or other building structure when the molding 1805 is attached to the wall (or structure). In one embodiment, an adhesive layer with a peel-off protective cover 2002 is provide to the back of the substrate. The adhesive can be used to attach the tape 2002 to a molding (or other building material) before the molding is installed.

Figure 21:
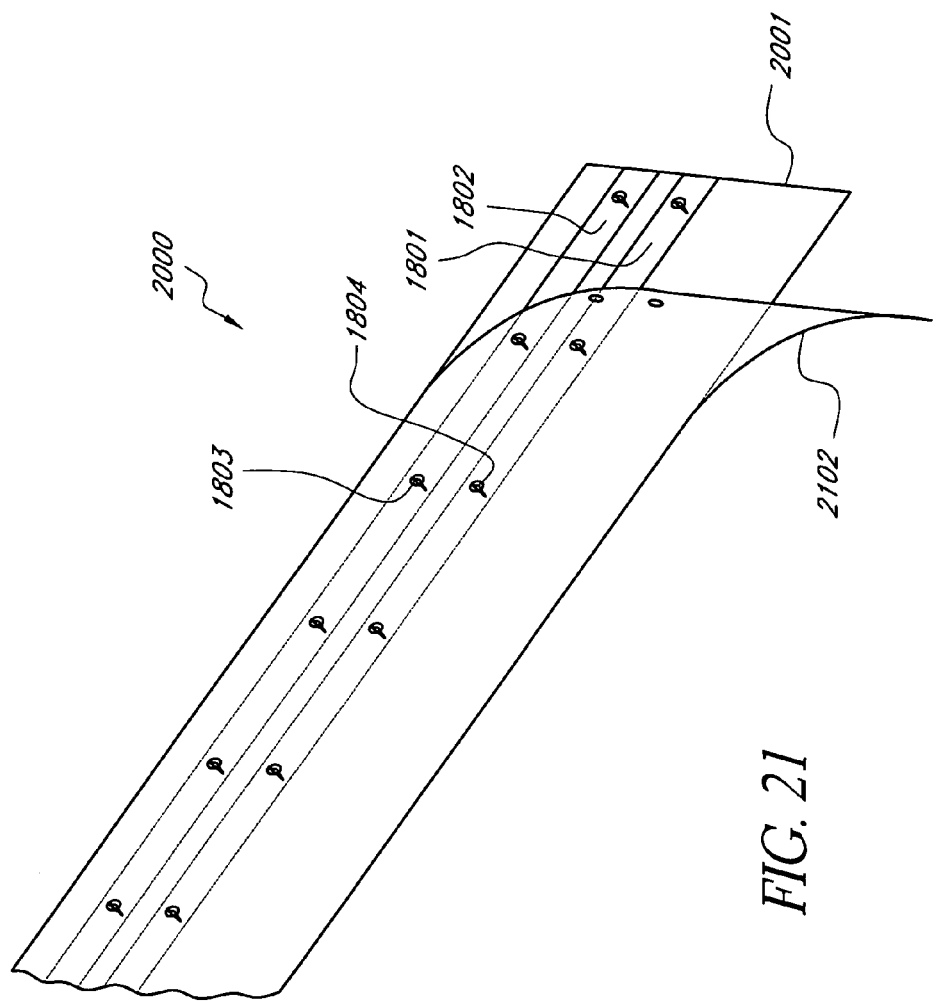
FIG. 21 shows an impedance probe configured for peel-and-stick application to a wall or other building material.

As shown in FIG. 21, an adhesive and a peel-off layer 2101 can also (either along with the adhesive and peel-off 2002 or in the alternative) be installed on the front of the tape 2000 to allow the tape 2000 to be installed before any covering of molding. Thus, the tape 2000 can also be installed to studs before drywall is installed, installed between studs, installed to flooring, attached to the inner surfaces of outer walls, etc.

Figure 22:
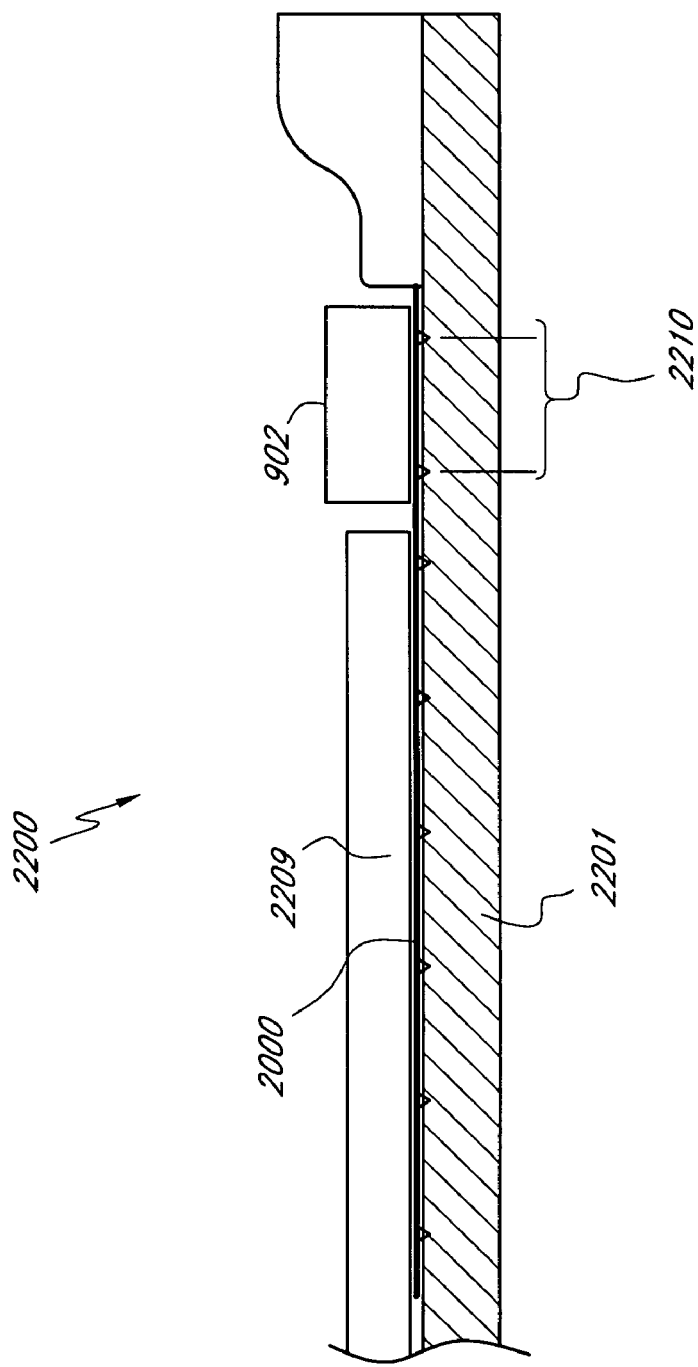
FIG. 22 shows one installation of the moisture sensor unit to an impedance probe provided between a wall or ceiling and a molding, wherein the sensor unit is mounted to the wall (or ceiling).

FIG. 22 shows one installation of the moisture sensor unit 902 to the impedance probe tape 2000 provided between a wall 2201 and a molding 2209. The sensor unit 902 is mounted to the wall and the tape 2000 is configured to extend past the end of the molding 2209 and under the sensor unit 902 (between the wall and the sensor unit 902). In one embodiment, a plurality of spikes or pins 2210 are provided to the sensor unit 902 to allow the sensor unit to make electrical contact with the conductors 1801, 1802 in the tape 2000.

Figure 23:
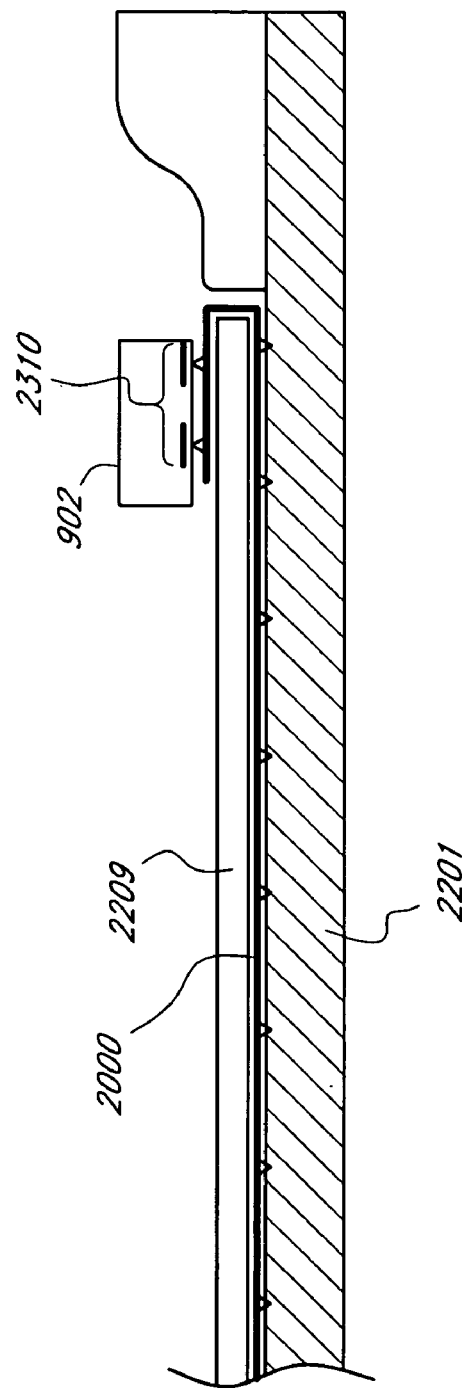
FIG. 23 shows one installation of the moisture sensor unit to an impedance probe provided between a wall or ceiling and a molding, wherein the sensor unit is mounted to the molding.

FIG. 23 shows an alternative installation of the moisture sensor unit 902 to the impedance probe tape 2000 provided between the wall 2201 and the molding 2209. In FIG. 23, the tape 2000 is configured to extend past the end of the molding 2209 and is wrapped around the end of the molding 2209 and onto the face of the molding 2209. The sensor unit 902 is mounted to the face of the molding with a portion of the tape 2000 between the sensor unit and the face of the molding. In one embodiment, one or more conductive pads 2310 are provided on the back of the sensor unit 902 to allow the sensor unit to make electrical contact with the conductors 1801, 1802 in the tape 2000 (and/or with the pins 1803, 1804).

Figure 24:
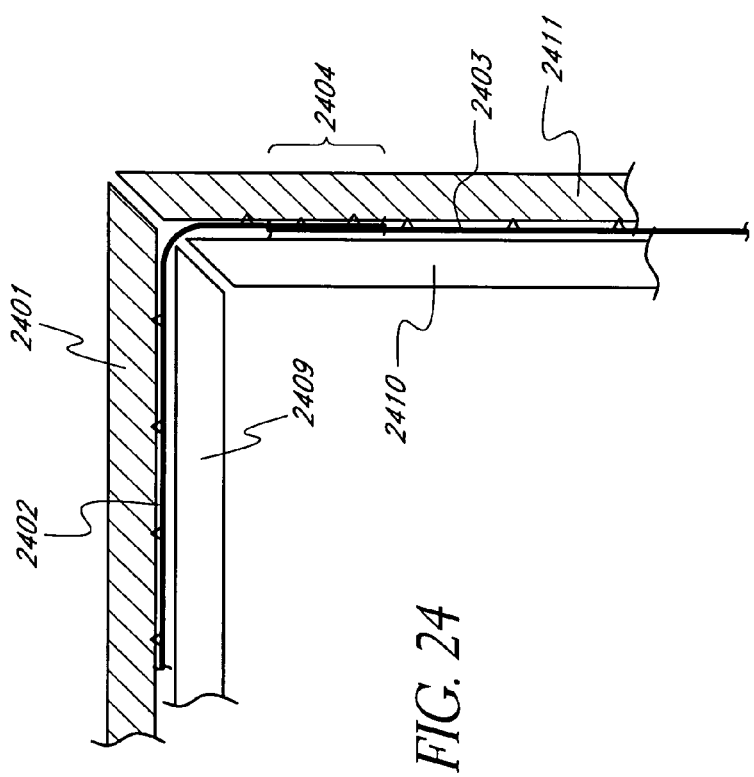
FIG. 24 shows the impedance probes from FIG. 20 or 21 wrapped around a corner.

FIG. 24 shows one example of an installation of the impedance probe tape 2000 wrapped around a corner. In FIG. 24 a first piece 2402 of impedance probe tape 2000 is mounted between a first section of wall 2401 and a first molding 2409. A second piece 2403 of impedance probe tape 2000 is mounted between a second section of wall 2411 and a second molding 2410. A portion of the first piece 2402 extends past the end of the molding 2409, wraps around the corner between the walls 2401 and 2411; and extends between the molding 2410 and the wall 2411. The piece 2402 overlaps the piece 2403 in a region 2404. Pins 1803, 1804 on the piece 2402 make electrical contact with the conductors 1801, 1802 on the piece 2403.

Figure 25:
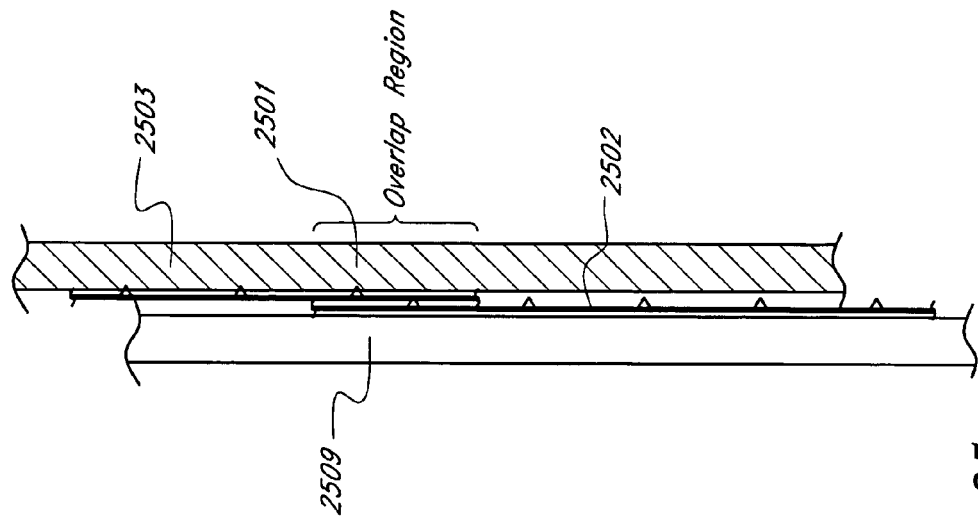
FIG. 25 shows the impedance probes from FIG. 20 or 21 overlapped to cover a longer area.

FIG. 25 shows one example of an installation of two shorter pieces of the impedance probe tape 2000 installed under a relatively long molding. In FIG. 25 a first piece 2503 of impedance probe tape 2000 is mounted between a wall 2501 and a molding 2509. A second piece 2502 of impedance probe tape 2000 is mounted between the wall 2501 and the molding 2509 such that a portion of the first piece 2503 overlaps a second piece 2502 in an overlap region. Pins 1803, 1804 on the piece 2502 make electrical contact with the conductors 1801, 1802 on the piece 2501.

Figure 26:
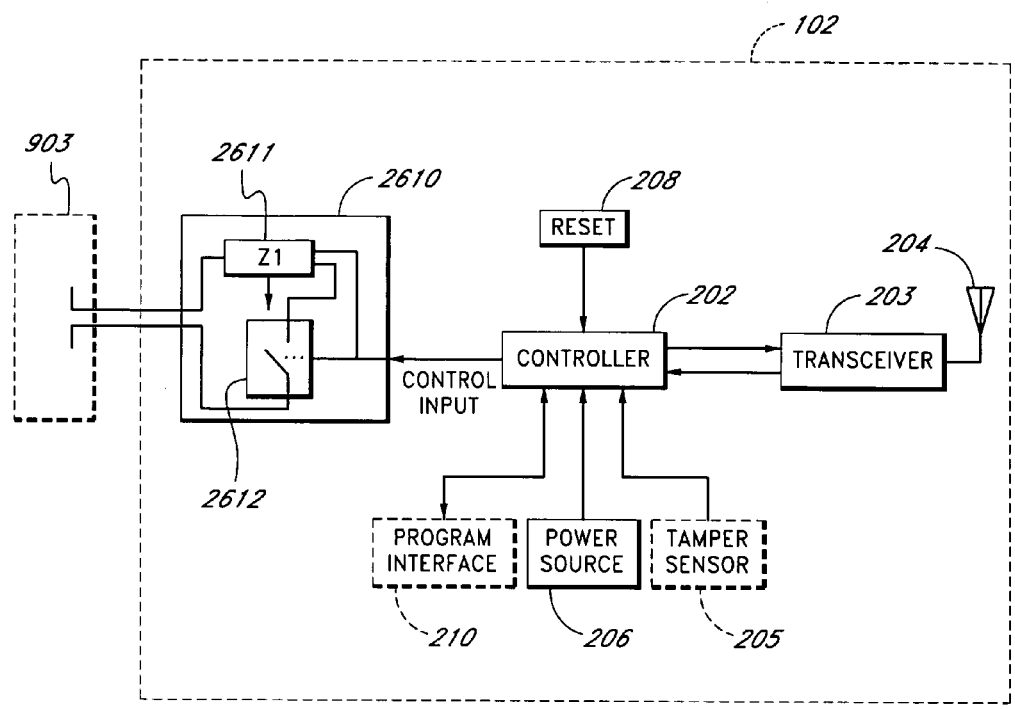
FIG. 26 shows a moisture sensor and a self-test sensor provided to a moisture probe.

FIG. 26 shows a self-test unit 2602 for use in connection with the moisture sensor unit 902. The self-test unit 2602 is similar to the moisture sensor unit 902 and includes the antenna 204, the transceiver 203, the controller 202, and the power source 206. A control input from the controller 202 is provided to a testing module 2610. The testing module 2610 includes a test impedance 2611 and an electronically-controlled switch 2612. The switch 2612 is configured to provide the test impedance 2611 to the impedance probe 903 when the switch 2612 is activated by the control input. In one embodiment, the control input can also be used to vary the impedance Z of the test impedance 2611. In one embodiment, the monitoring system 113 sends instructions to the self-test unit 2602 to control the impedance Z of the test impedance 2611.

When instructed, the self-test unit 2602 connects the test impedance 2611 to the impedance probe 903. The moisture sensor 902, also provided to the impedance probe 903, can then be used to measure the impedance of the impedance probe. The moisture sensor 902 can expect to measure the an impedance corresponding to the combination of the impedance Z and the impedance of the probe just before or after the self-test unit provided the test impedance Z to the probe 903. Thus, for example, in one embodiment, the sensor unit 902 is be provided to one end of the impedance probe tape 2000 and the self-test unit 2602 is provided at an opposite end of the impedance probe tape 2000 to facilitate testing of the tape 2000 and/or to facilitate testing of the moisture sensor unit 902.

It will be evident to those skilled in the art that the invention is not limited to the details of the foregoing illustrated embodiments and that the present invention may be embodied in other specific forms without departing from the spirit or essential attributed thereof; furthermore, various omissions, substitutions and changes may be made without departing from the spirit of the inventions. For example, although specific embodiments are described in terms of the 900 MHz frequency band, one of ordinary skill in the art will recognize that frequency bands above and below 900 MHz can be used as well. The wireless system can be configured to operate on one or more frequency bands, such as, for example, the HF band, the VHF band, the UHF band, the Microwave band, the Millimeter wave band, etc. One of ordinary skill in the art will further recognize that techniques other than spread spectrum can also be used and/or can be used instead of spread spectrum. The modulation use is not limited to any particular modulation method, such that modulation scheme used can be, for example, frequency modulation, phase modulation, amplitude modulation, combinations thereof, etc. The foregoing description of the embodiments is, therefore, to be considered in all respects as illustrative and not restrictive, with the scope of the invention being delineated by the appended claims and their equivalents.

What is claimed is:

1. A moisture sensor system, comprising:
 a sensor unit comprising a moisture sensor provided to a moisture probe, said sensor unit configured to receive instructions, said sensor unit configured to report a severity of a moisture level when said sensor unit determines that data measured by said moisture sensor fails a threshold test, said sensor unit configured to adjust said threshold according to sensor reading taken during a specified time period, wherein said threshold is computed as an average of a plurality of sensor data values.

2. A moisture sensor system, comprising:
 a sensor unit comprising a moisture sensor provided to a moisture probe, said sensor unit configured to receive instructions, said sensor unit configured to report a severity of a moisture level when said sensor unit determines that data measured by said moisture sensor fails a threshold test, said sensor unit configured to adjust said threshold according to sensor reading taken during a specified time period, wherein said threshold is computed at least in part as a weighted average of a plurality of sensor data values.

3. A moisture sensor system, comprising:
 a sensor unit comprising a moisture sensor provided to a moisture probe, said sensor unit configured to receive instructions, said sensor unit configured to report a severity of a moisture level when said sensor unit determines that data measured by said moisture sensor fails a threshold test, said sensor unit configured to adjust said threshold according to sensor reading taken during a specified time period, wherein said severity is computed according to how far a sensor reading has risen above said threshold.

4. A moisture sensor system, comprising:
 a sensor unit comprising a moisture sensor provided to a moisture probe, said sensor unit configured to receive instructions, said sensor unit configured to report a severity of a moisture level when said sensor unit determines that data measured by said moisture sensor fails a threshold test, said sensor unit configured to adjust said threshold according to sensor reading taken during a specified time period, wherein said severity is computed at least in part as a function of how far and how rapidly sensor readings have risen above said threshold value.

5. A moisture sensor system, comprising:
 a sensor unit comprising a moisture sensor provided to a moisture probe, said sensor unit configured to receive instructions, said sensor unit configured to report a severity of a moisture level when said sensor unit determines that data measured by said moisture sensor fails a threshold test, said sensor unit configured to adjust said threshold according to sensor reading taken during a specified time period, wherein said severity is computed at least in part as a function of how many sensor readings have been measured above said threshold value.

6. A moisture sensor system, comprising:
 a sensor unit comprising a moisture sensor provided to a moisture probe, said sensor unit configured to receive instructions, said sensor unit configured to report a severity of a moisture level when said sensor unit determines that data measured by said moisture sensor fails a threshold test, said sensor unit configured to adjust said threshold according to sensor reading taken during a specified time period, wherein said severity is computed as a function of what percentage of recent sensor readings have been measured above said threshold value.

7. The system of claim 1, further comprising means for wirelessly transmitting data from said moisture sensor to a monitoring station.

8. The system of claim 1, further comprising means for wirelessly transmitting resistance data to a monitoring station.

9. The system of claim 1, further comprising means for receiving instructions to close a water shutoff valve.

10. The system of claim 1, wherein said sensor unit is configured as a wireless sensor unit configured to report ditai measured by said moisture sensor when said wireless sensor determines that said moisture data fails a threshold test, said wireless sensor unit configured to operating in a low-power mode when not transmitting or receiving data.

11. The system of claim 1, further comprising a self-test module.

12. The system of claim 11, wherein said self-test module provides a resistor to said first and second conductors.

13. The system of claim 1, further comprising a monitoring computer configured to attempt to contact a responsible party by telephone.

14. The system of claim 1, further comprising a monitoring computer configured to attempt to contact a responsible party by cellular telephone.

15. The system of claim 1, further comprising a monitoring computer configured to attempt to contact a responsible party by cellular text messaging.

16. The system of claim 1, further comprising a monitoring computer configured to attempt to contact a responsible party by pager.

17. The system of claim 1, further comprising a monitoring computer configured to attempt to contact a responsible party by Internet.

18. The system of claim 1, further comprising a monitoring computer configured to attempt to contact a responsible party by email.

19. The system of claim 1, further comprising a monitoring computer configured to attempt to contact a responsible party by Internet instant messaging.

20. The system of claim 1, further comprising a monitoring computer is configured to provide plots of moisture levels.

21. The system of claim 1, wherein said system is configured to receive an instruction to change a status reporting interval.

22. The system of claim 1, wherein said system is configured to receive an instruction to change a sensor data reporting interval.

23. The system of claim 1, wherein a monitoring computer is configured to monitor a status of said sensor unit.

24. The moisture sensor system of claim 1, wherein said severity of a moisture level depends at least in part on a length of time said moisture sensor has detected moisture above a threshold level.

25. The moisture sensor system of claim 1, wherein said severity of a moisture level depends at least in part on a rate of raise in said moisture level.

26. The sensor system of claim 1, said moisture probe comprising:
   a first probe comprising a first conductor with a plurality of pins;
   a second probe comprising a second conductor with a plurality of pins; and
   a substrate provided to said first probe and said second probe, said moisture sensor configured to measure an impedance between said first probe and said second probe.

27. The system of claim 26, wherein said impedance comprises a resistance.

28. The system of claim 26, wherein said impedance comprises a reactance.

29. The system of claim 26, wherein said first and second conductors are substantially linear.

30. The system of claim 26, wherein said first and second conductors are substantially linear and attached to said substrate in a substantially parallel alignment.

31. The system of claim 26, wherein a peel-and-stick adhesive is provided to said substrate.

32. The system of claim 26, wherein an adhesive is provided to a back side of said substrate.

33. The system of claim 26, wherein an adhesive is provided to a front side of said substrate and wherein said first and second conductors are provided to said front side of said substrate.

34. The system of claim 26, wherein said sensor unit configured as a wireless sensor unit configured to report data measured by said moisture sensor when said wireless sensor determines that said moisture data fails a threshold test, said wireless sensor unit configured to operating in a low-power mode when not transmitting or receiving data.

35. The system of claim 26 wherein said substrate comprises a baseboard molding.

36. The system of claim 26, wherein said substrate comprises a wall molding.

* * * * *

UNITED STATES PATENT AND TRADEMARK OFFICE
CERTIFICATE OF CORRECTION

PATENT NO. : 7,142,123 B1  Page 1 of 1
APPLICATION NO. : 11/233931
DATED : November 28, 2006
INVENTOR(S) : Lawrence Kates It is certified that error appears in the above-identified patent and that said Letters Patent is hereby corrected as shown below:

In column 5 at line 14, change "clamp" to --damp--.

In column 16 at line 50, change "fimgus" to --fungus--.

In column 27 at line 10, in Claim 10, change "ditai" to --data--.

In column 28 at line 43, in Claim 35, after "claim 26" insert --,--.

Signed and Sealed this

Sixteenth Day of October, 2007

JON W. DUDAS
*Director of the United States Patent and Trademark Office*